US012678518B2

(12) United States Patent
Mi et al.

(10) Patent No.: US 12,678,518 B2
(45) Date of Patent: Jul. 14, 2026

(54) THERANOSTIC PROBE AND ITS USE FOR TARGETING AND/OR LABELING THE EGFR KINASE AND/OR THE CELLS EXPRESSING EGFR OR ITS FAMILY MEMBERS

(71) Applicant: Tianjin University, Tianjin (CN)

(72) Inventors: Lizhi Mi, Tianjin (CN); Xingxing Wang, Tianjin (CN); Peng Liu, Tianjin (CN); Xiaohong Qin, Tianjin (CN); Zhiqun Shang, Tianjin (CN)

(73) Assignee: Tianjin University, Tianjin (CN)

( * ) Notice: Subject to any disclaimer, the term of this patent is extended or adjusted under 35 U.S.C. 154(b) by 1156 days.

(21) Appl. No.: 17/756,689

(22) PCT Filed: Feb. 21, 2020

(86) PCT No.: PCT/CN2020/076209
§ 371 (c)(1),
(2) Date: May 31, 2022

(87) PCT Pub. No.: WO2020/169085
PCT Pub. Date: Aug. 27, 2020

(65) Prior Publication Data
US 2023/0085980 A1 Mar. 23, 2023

(30) Foreign Application Priority Data
Feb. 21, 2019 (WO) ................ PCT/CN2019/075751

(51) Int. Cl.
*A61K 49/00* (2006.01)
*G01N 33/574* (2006.01)

(52) U.S. Cl.
CPC ...... *A61K 49/0032* (2013.01); *A61K 49/0052* (2013.01); *G01N 33/57434* (2013.01)

(58) Field of Classification Search
CPC ........... A61K 49/0032; A61K 49/0052; G01N 33/57434; C07D 403/14; A61P 35/00
See application file for complete search history.

(56) References Cited

U.S. PATENT DOCUMENTS

2013/0280279 A1* 10/2013 Brinkmann ............. A61P 29/00
530/391.9

FOREIGN PATENT DOCUMENTS

| | | | |
|---|---|---|---|
| CN | 103333246 | A | 10/2013 |
| CN | 104212440 | A | 12/2014 |
| WO | 2015151081 | A2 | 10/2015 |

OTHER PUBLICATIONS

Blair et al., "Structure-guided development of affinity probes for tyrosine kinases using chemical genetics," Nature Chemical Biology 3(4):229-238 (2007).
Mishani et al., "Novel carbon-11 labeled 4-dimethylamino-but-2-enoic acid [4-(phenylamino)-quinazoline-6-yl]-amides: potential PET bioprobes for molecular imaging of EGFR-positive tumors," Nuclear Medicine and Biology 31:469-476 (2004).
Weitsman, G. et al. "Detecting intratumoral heterogeneity of EGFR activity by liposome-based in vivo transfection of a fluorescent biosensor," Oncogene, vol. 36 (Feb. 6, 2017) pp. 3618-3628.
International Search Report (Form PCT/ISA/210) for International Patent Application No. PCT/CN2020/076209, issued from the International Searching Authority, date of mailing May 21, 2020, 4 pages.
Written Opinion of the International Searching Authority (Form PCT/ISA/237) for International Patent Application No. PCT/CN2020/076209, issued from the International Searching Authority, date of mailing May 21, 2020, 4 pages.
International Preliminary Report on Palatability (Form PCT/IB/373) for International Patent Application No. PCT/ CN2020/076209, issued from the International Bureau of WIPO, date of mailing Aug. 10, 2021, 5 pages.

* cited by examiner

*Primary Examiner* — Robert S Cabral
(74) *Attorney, Agent, or Firm* — Ice Miller LLP

(57) ABSTRACT

The present application is directed to a theranostic probe and its use for targeting and/or labeling the EGFR kinase and/or the cells expressing EGFR or its family members.

9 Claims, 8 Drawing Sheets

Specification includes a Sequence Listing.

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: EGFR-Forward

<400> SEQUENCE: 1

cccactcatg ctctacaacc c                                         21


<210> SEQ ID NO 2
<211> LENGTH: 21
<212> TYPE: DNA
<213> ORGANISM: Artificial Sequence
<220> FEATURE:
<223> OTHER INFORMATION: EGFR-Reverse

<400> SEQUENCE: 2
```

-continued tcgcacttct tacacttgcg g 21

<210> SEQ ID NO 3
<211> LENGTH: 22
<212> TYPE: DNA
<213> ORGANISM: Artificial Sequence
<220> FEATURE:
<223> OTHER INFORMATION: HER2-Forward

<400> SEQUENCE: 3
tgtgactgcc tgtccctaca ac 22

<210> SEQ ID NO 4
<211> LENGTH: 20
<212> TYPE: DNA
<213> ORGANISM: Artificial Sequence
<220> FEATURE:
<223> OTHER INFORMATION: HER2-Reverse

<400> SEQUENCE: 4
ccagaccata gcacactcgg 20

<210> SEQ ID NO 5
<211> LENGTH: 20
<212> TYPE: DNA
<213> ORGANISM: Artificial Sequence
<220> FEATURE:
<223> OTHER INFORMATION: Beta-actin-Forward

<400> SEQUENCE: 5
gggacctgac tgactacctc 20

<210> SEQ ID NO 6
<211> LENGTH: 20
<212> TYPE: DNA
<213> ORGANISM: Artificial Sequence
<220> FEATURE:
<223> OTHER INFORMATION: Beta-actin-Reverse

<400> SEQUENCE: 6
tcatactcct gcttgctgat 20

<210> SEQ ID NO 7
<211> LENGTH: 20
<212> TYPE: DNA
<213> ORGANISM: Artificial Sequence
<220> FEATURE:
<223> OTHER INFORMATION: GAPDH-Forward

<400> SEQUENCE: 7
atcatccctg cctctactgg 20

<210> SEQ ID NO 8
<211> LENGTH: 20
<212> TYPE: DNA
<213> ORGANISM: Artificial Sequence
<220> FEATURE:
<223> OTHER INFORMATION: GAPDH-Reverse

<400> SEQUENCE: 8
gtcaggtcca ccactgacac 20

THERANOSTIC PROBE AND ITS USE FOR TARGETING AND/OR LABELING THE EGFR KINASE AND/OR THE CELLS EXPRESSING EGFR OR ITS FAMILY MEMBERS

CROSS-REFERENCE TO RELATED APPLICATION

This application is a Section 371 of International Application No. PCT/CN2020/076209, filed on Feb. 21, 2020, which published in the English language on Aug. 27, 2020, under International Publication No. WO 2020/169085 A1, which claims priority to PCT/CN2019/075751, filed on Feb. 21, 2019. Each disclosure is incorporated herein by reference in its entirety.

REFERENCE TO SEQUENCE LISTING SUBMITTED ELECTRONICALLY

This application contains a sequence listing, which is submitted electronically via the Patent Office electronic filing system (EFS) as an ASCII formatted sequence listing with a file name "065824.16US1 Sequence Listing" and creation date of Jan. 27, 2026 and having a size of 1,876 bytes. The sequence listing submitted via EFS is part of the specification and is herein incorporated by reference in its entirety.

TECHNICAL FIELD

The present application is directed to a theranostic probe and its use for targeting and/or labeling the EGFR kinase and/or the cells expressing EGFR or its family members.

BACKGROUND

It was estimated that 9.6 million patients worldwide would die from cancer in 2018[1]. The life quality and expectation of these patients would be greatly improved, if the occurrence or the resurrection of cancers could be diagnosed in the earlier phases of oncogenesis. For this reason, liquid biopsy techniques, which extract pathological information from the blood or body liquid of the patient, have been quickly developed in recent years[2-5]. Compared with the traditional tissue biopsy, liquid biopsy is non-invasive and cost-efficient, and thus could be repeatedly performed in tracing cancer progression, especially for those physically or economically challenged patients with severe complications.

Liquid biopsy relies on the detection of oncogenic biomarkers, including circulating tumor DNA, circulating tumor cells, or overexpressed protein markers[2-6]. Currently, in the detection of CTCs, tumor cells were enriched either by immuno-sorting or by microfluidic chips[2-4]. Those enriched cells were then individually sequenced to identify the genetic, epigenetic, or translational variations associated with cancers. This two-step strategy could be generally applied in the diagnosis of various cancers[2-5]. But it lacks specificity and efficiency, especially in the cases that the oncogenic marker has already been identified. On the other hand, the antibodies currently used in immuno-sorting of CTCs were often selected for their abilities to target antigens widely expressed on many different cancers[3-5]. However, these antibodies were not competent for reporting the status of intracellular mutation nor the conformation of a specific biomarker associated oncogenesis. Such mutational or conformational status is often critical in the selection of therapeutic window and in the determination of drug resistance[7-10].

For example, about 20% of non-small cell lung cancer (NSCLC) tumors are associated with mutations in the intracellular kinase domain of the EGF receptor[11, 12]. The efficacies of EGFR-targeted inhibitors are often sensitive to the mutational status of the kinase[9, 10]. In addition, secondary mutation on the EGFR kinase will cause resistance to these inhibitors[7, 8]. Therefore, it is necessitated to develop new methodology, which could efficiently enrich tumor cells and report the mutational status of an oncogenic biomarker for diagnosis and treatment.

EGF receptor, in together with its homologs HER2, HER3, and HER4, belongs to the receptor tyrosine kinase superfamily[13, 14]. In these receptors, the conformation and corresponding activity of the intracellular kinase are regulated by ligand-induced dimerization[13, 14]. In the absence of ligands, the EGF receptor kinase domain adopts an inactive state (FIG. 1A, left panel), in which the α-C helix is positioned away from the active site and the activation loop is bent over toward the kinase hinge to exclude substrate binding[15, 16]. In ligand-bound, dimeric receptors, one kinase, served as an activator, stabilizes the other in an activated state by forming cyclin/CDK-like asymmetric dimer (FIG. 1A, right panel)[15, 16] The activated kinase is characterized by its inward α-C helix and extended activation loop for substrate binding and phosphorylation. Oncogenic mutations or over-expression of the EGF receptor alters the kinase activity by destabilizing the kinase inactive conformation, stabilizing its active conformation, or both (FIG. 1A)[17]. As some EGFR kinase inhibitors, including gefitinib and PD168393, are very sensitive to the oncogenic mutation of the receptor, potentially, they could be employed in reporting the kinase mutational or conformational status.

Prostate cancer is one of the leading causes of death of men from cancers over the world[31, 32]. In 2018, it was estimated that more than 1.2 million men had been diagnosed with prostate cancer and over 359,000 patients died from the disease worldwide[31]. As with many other cancers, the survival and life quality of prostate cancer patients would be improved, if early diagnosis of the disease and close monitoring of the disease progression and therapeutic response could be easily and routinely performed[31].

Currently, ultrasound or MRI guided needle biopsy is still the gold standard in the diagnosis of prostate cancer[33, 34]. Tissue specimens are collected from multiple spots on the prostate and examined by various tissue staining methods. However, this invasive procedure may not only cause complicated side effects, but also could not fully capture the lesion distribution and the status of cancer progression[35]. As such, liquid biopsy techniques, which extract pathological information from the blood or body liquid of the patient, have been quickly developed in recent years[35-40].

Liquid biopsy relies on the detection of oncogenic biomarkers, including circulating tumor DNA, circulating tumor cells (CTCs), or overexpressed protein markers[36-39, 41]. Currently, in the detection of CTCs, tumor cells were enriched either by immuno-sorting or by microfluidic chips[36-38]. Those enriched cells were then sequenced to identify the genetic, epigenetic, or translational variations associated with cancers[36-39]. However, the antibodies currently used in immuno-sorting of CTCs were often selected for their abilities to target antigens widely expressed on various cancers[37-39]. These antibodies were not competent for reporting the status of intracellular mutations nor the conformations of a specific biomarker associated with oncogenesis. Such mutational or conformational status is often critical in the selection of therapeutic window and in the determination of drug resistance[42-45]. Therefore, it is necessitated to develop new methodology, which could efficiently enrich tumor cells and report the mutational status of an oncogenic biomarker for diagnosis and treatment[40].

On the other hand, expression or mutation profiling of tumor cells could not be translated directly into therapeutic response, and thus clinical trials designed based on those profilings might fail in practice. For example, EGFR overexpression had been observed in over one-third of prostate cancer patients and had been linked to the biochemical relapse and hormone-refractory status of the cancer[46, 47]. In addition, it had been reported that EGFR mutations were associated with accelerated progression of prostate cancer to hormone-refractory state[48]. The intriguing linkage between EGFR malfunctions and prostate cancer progression provoked clinical investigations of EGFR inhibitors in the treatment of hormone-refractory or hormone naive patients with EGFR overexpression 4'. However, multicenter clinical studies of EGFR inhibitors failed to demonstrate their efficacies in the treatment of these populations[49], suggesting further clarification of the pathogenic basis or development of better stratification strategies are required.

Summary of the Present Application

Herein, we reported our structure-based modular design of theranostic probes targeting EGFR in specific conformations. We demonstrated examples of using such a probe in screening inhibitors by competition, in sorting cells with over-expressed or mutated EGFR, and in imaging of EGFR interactions on the cell surface. Surprisingly, we found that PD168393 was more reactive to a kinase dimeric state distinguished from that active, asymmetric dimer.

Herein, we also designed an irreversible, modular fluorescent probe targeting oncogenic epidermal growth factor (EGF) receptor (EGFR) kinase. This probe could specifically inhibit EGFR kinase activity in a dose-dependent manner, selectively label the cells overexpressing EGFR in flowcytometry, sensitively bind to EGFR oncogenic mutants, and preferentially bind to an intermediate kinase dimer distinguished from its active, asymmetric dimer.

In the first aspect, the present application provides a theranostic probe represented by formula (1):

Module 2-L-Module 1 (1)

wherein

L is a linker;

Module 1 is a moiety targeting the EGFR kinase; and

Module 2 is an imaging probe selected from the group consisting of fluorescent, MRI and radioactive probes;

or a theranostically acceptable salt thereof.

In an embodiment of the first aspect, L is —C(O)O— or —C(O)NH—.

In another embodiment of the first aspect, Module 1 is an inhibitor against the EGFR kinase.

In another embodiment of the first aspect, Module 1 is represented by formula (2):

(2)

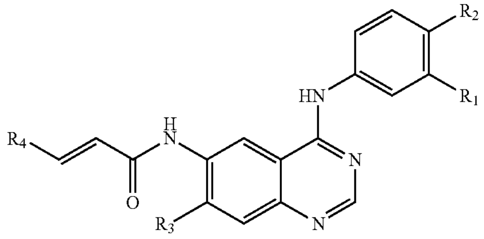

wherein $R_1$ in formula (2) is H, halogen (e.g. F, Cl or Br) or $C_{2-6}$alkynyl (e.g. ethenyl);

$R_2$ in formula (2) is H, halogen (e.g. F, Cl or Br), $C_{6-10}$aryl$C_{1-6}$alkyloxy (e.g. phenylmethyloxy) or 5- to 6-membered heteroaryl$C_{1-6}$alkyloxy (e.g. pyridinylmethyloxy, especially pyridin-2-ylmethyloxy), wherein the $C_{6-10}$aryl and 5- to 6-membered heteroaryl are optionally substituted with halogen (e.g. F, Cl or Br) (e.g. $R_2$ in formula (2) is 3-fluorophenylmethyloxy), and the 5- to 6-membered heteroaryl comprises 1, 2, 3 or 4 heteroatoms selected from the group consisting of O, S and N;

$R_3$ in formula (2) is H, $C_{1-6}$alkyloxy optionally substituted with $C_{1-6}$alkyloxy (e.g. $R_3$ in formula (2) is methyloxy, ethyloxy or methyloxyethyloxy), or 5- to 6-membered heterocycloalkyloxy (e.g. tetrahydrofuranyloxy, especially tetrahydrofuran-3-yloxy), wherein the 5- to 6-membered heterocycloalkyl comprises 1 or 2 heteroatoms selected from the group consisting of O, S and N;

$R_4$ in formula (2), as the attachment point of Module 1 to L, is $—(CH_2)_n—$; and n in formula (2) is 0, 1, 2, 3, 4, 5 or 6.

In another embodiment of the first aspect, Module 2 is represented by formula (3) or (4):

(3)

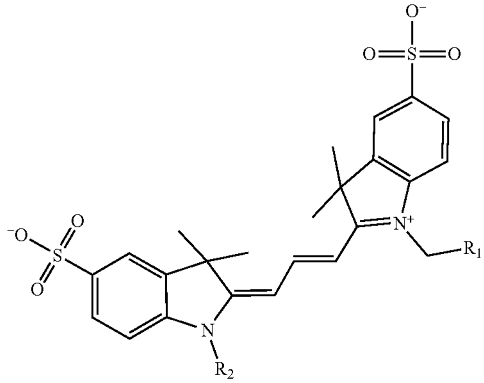

-continued (4)

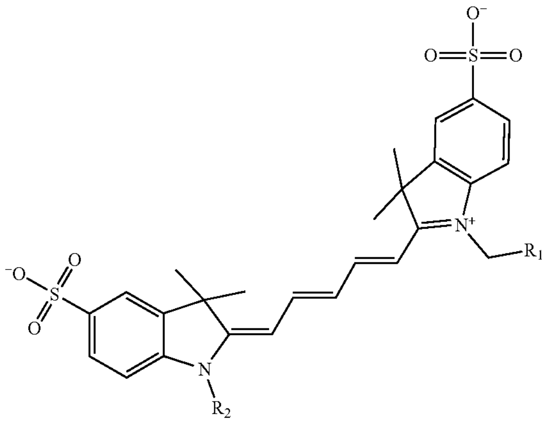

wherein $R_1$ in formula (3) or (4), as the attachment point of Module 2 to L, is $-(CH_2)_n-$;

$R_2$ in formula (3) or (4) is $-(CH_2)_nCH_3$; and n in formula (3) or (4), at each occurrence, is independently 0, 1, 2, 3, 4, 5 or 6;

or Module 2 is represented by formula (5) or (6):

$$^{18}FCH_2-(CH_2)_n-*$$ (5)

(6)

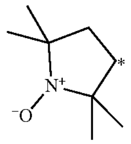

wherein the symbol * in formula (5) or (6) represents the attachment point of Module 2 to L; and n in formula (5) is independently 0, 1, 2, 3, 4, 5 or 6;

wherein if necessary, a counterion is present and selected from the group consisting of alkali metal and alkaline earth metal ions, especially a sodium, potassium, calcium or magnesium ion.

In another embodiment of the first aspect, the theranostic probe is represented by formula (7):

(7)

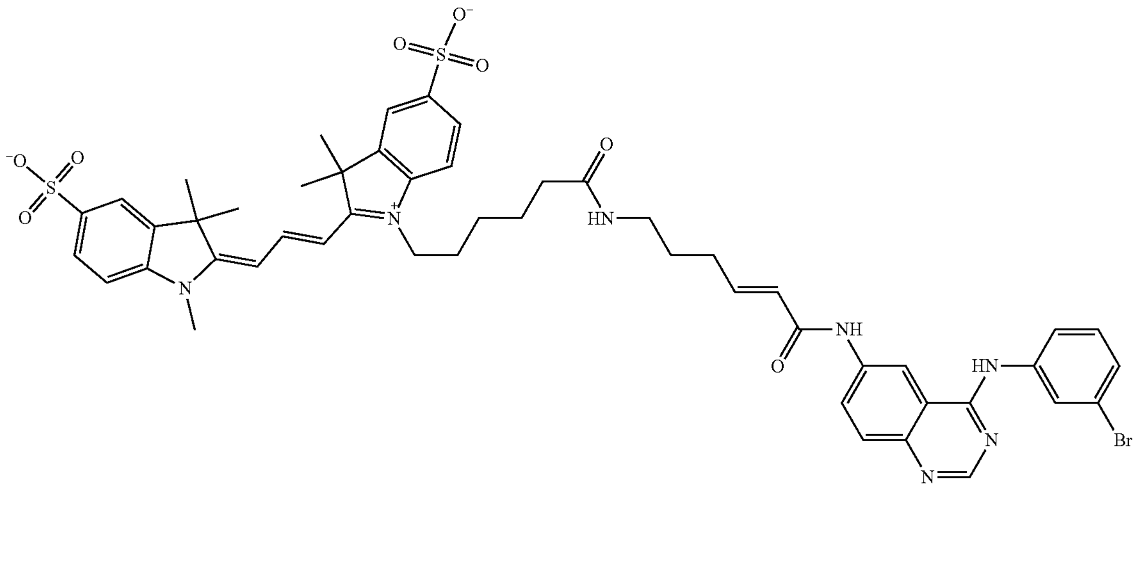

which is also called PDCy3 or Compound 2 herein, wherein if necessary, a counterion is present and selected from the group consisting of alkali metal and alkaline earth metal ions, especially a sodium, potassium, calcium or magnesium ion.

In another embodiment of the first aspect, the EGFR kinase is a wild type.

In another embodiment of the first aspect, the EGFR kinase has a mutation of L834R.

In another embodiment of the first aspect, the EGFR kinase has a mutation of V924R.

In another embodiment of the first aspect, the EGFR kinase has a mutation of V745M.

In another embodiment of the first aspect, the EGFR kinase has a mutation of combination of any two or three of L834R, V924R and V745M, such as combination of L834R with V924R.

In another embodiment of the first aspect, the EGFR kinase is present in a dimeric conformation.

In another embodiment of the first aspect, the EGFR kinase is present in a dimeric conformation formed from the EGFR kinase of a wild type.

In another embodiment of the first aspect, the EGFR kinase is present in a dimeric conformation formed from the EGFR kinase having a mutation of L834R.

In another embodiment of the first aspect, the EGFR kinase is present in a dimeric conformation formed from the EGFR kinase having a mutation of V924R.

In another embodiment of the first aspect, the EGFR kinase is present in a dimeric conformation formed from the EGFR kinase having a mutation of V745M.

In another embodiment of the first aspect, the EGFR kinase is present in a dimeric conformation formed from the EGFR kinase having a mutation of combination of any two or three of L834R, V924R and V745M, such as combination of L834R with V924R.

In another embodiment of the first aspect, the EGFR kinase is associated with oncogenesis, preferably prostate cancer, and more preferably metastatic and/or castration-resistant prostate cancer.

In another embodiment of the first aspect, the conformation of the EGFR kinase is associated with oncogenesis, preferably prostate cancer, and more preferably metastatic and/or castration-resistant prostate cancer.

In the second aspect, the present application provides use of the theranostic probe as defined in the first aspect for targeting and/or labeling the EGFR kinase and/or the cells expressing EGFR or its family members.

In an embodiment of the second aspect, the theranostic probe as defined in the first aspect is used for targeting and/or labeling the EGFR kinase. In another embodiment of the second aspect, the theranostic probe as defined in the first aspect is used for targeting and/or labeling the EGFR kinase in a high throughput screening platform. In an embodiment of the second aspect, the high throughput screening platform is used for developing an inhibitor against EGFR.

In another embodiment of the second aspect, the theranostic probe as defined in the first aspect is used for targeting and/or labeling the cells expressing EGFR or its family members. In another embodiment of the second aspect, the theranostic probe as defined in the first aspect is used for targeting and/or labeling the cells expressing EGFR or its family members in a liquid biopsy. In another embodiment of the second aspect, the liquid biopsy is non-invasive. In another embodiment of the second aspect, the liquid biopsy is used to detect tumor cell in blood and/or body fluid. In another embodiment of the second aspect, the liquid biopsy is used to determine overexpression of EGFR, oncogenic mutation of EGFR and/or drug resistance of tumor cell due to the mutation. In another embodiment of the second aspect, the use is for targeting and/or labeling the cells expressing EGFR or its family members in a sample. In another embodiment of the second aspect, the sample is body fluid (such as blood or urine) or biopsy tissue. In another embodiment of the second aspect, the sample is urine.

In another embodiment of the second aspect, the targeting and/or labeling are conducted by the following steps:

mixing the EGFR kinase and/or the cells expressing EGFR or its family members with the theranostic probe; and determining the binding level therebetween.

In another embodiment of the second aspect, the EGFR kinase is a wild type.

In another embodiment of the second aspect, the EGFR kinase has a mutation of L834R.

In another embodiment of the second aspect, the EGFR kinase has a mutation of V924R.

In another embodiment of the second aspect, the EGFR kinase has a mutation of V745M.

In another embodiment of the second aspect, the EGFR kinase has a mutation of combination of any two or three of L834R, V924R and V745M, such as combination of L834R with V924R.

In another embodiment of the second aspect, the EGFR kinase is present in a dimeric conformation.

In another embodiment of the second aspect, the EGFR kinase is present in a dimeric 30 conformation formed from the EGFR kinase of a wild type.

In another embodiment of the second aspect, the EGFR kinase is present in a dimeric conformation formed from the EGFR kinase having a mutation of L834R.

In another embodiment of the second aspect, the EGFR kinase is present in a dimeric conformation formed from the EGFR kinase having a mutation of V924R.

In another embodiment of the second aspect, the EGFR kinase is present in a dimeric conformation formed from the EGFR kinase having a mutation of V745M.

In another embodiment of the second aspect, the EGFR kinase is present in a dimeric conformation formed from the EGFR kinase having a mutation of combination of any two or three of L834R, V924R and V745M, such as combination of L834R with V924R.

In another embodiment of the second aspect, the EGFR kinase is associated with oncogenesis, preferably prostate cancer, and more preferably metastatic and/or castration-resistant prostate cancer.

In another embodiment of the second aspect, the conformation of the EGFR kinase is associated with oncogenesis, preferably prostate cancer, and more preferably metastatic and/or castration-resistant prostate cancer.

In the third aspect, the present application provides use of the theranostic probe as defined in the first aspect in a liquid biopsy.

In an embodiment of the third aspect, the liquid biopsy is non-invasive.

In another embodiment of the third aspect, the liquid biopsy is used to detect tumor cell in blood and/or body fluid.

In another embodiment of the third aspect, the liquid biopsy is used to determine overexpression of EGFR, oncogenic mutation of EGFR and/or drug resistance of tumor cell due to the mutation.

In the fourth aspect, the present application provides use of the theranostic probe as defined in the first aspect in a high throughput screening platform.

In an embodiment of the fourth aspect, the high throughput screening platform is used for developing an inhibitor against EGFR.

In the fifth aspect, the present application provides use of the theranostic probe as defined in the first aspect for stratification of a patient suffering from a cancer expressing EGFR.

In an embodiment of the fifth aspect, the cancer is prostate cancer. In another embodiment of the fifth aspect, the cancer is metastatic and/or castration-resistant prostate cancer.

In another embodiment of the fifth aspect, the EGFR has a mutation of V745M.

In another embodiment of the fifth aspect, the EGFR is present in a dimeric conformation.

In another embodiment of the fifth aspect, the EGFR is present in a dimeric conformation formed from the EGFR having a mutation of V745M.

In another embodiment of the fifth aspect, the stratification is conducted by the following steps:

mixing a sample from the patient with the theranostic probe; and determining the binding level therebetween.

In another embodiment of the fifth aspect, the sample is body fluid (such as blood or urine) or biopsy tissue. In another embodiment of the fifth aspect, the sample is urine.

In the sixth aspect, the present application provides use of the theranostic probe as defined in the first aspect in a high throughput screening platform.

In an embodiment of the sixth aspect, the high throughput screening platform is used for developing an inhibitor against EGFR.

In another embodiment of the sixth aspect, the EGFR kinase is a wild type. In another embodiment of the sixth aspect, the EGFR kinase has a mutation of L834R, V924R, V745M or combination of any two or three of L834R, V924R and V745M, such as combination of L834R with V924R.

In another embodiment of the sixth aspect, the EGFR kinase is present in a dimeric conformation. In another embodiment of the sixth aspect, the EGFR kinase is present in a dimeric conformation formed from the EGFR kinase of a wild type. In another embodiment of the sixth aspect, the EGFR kinase is present in a dimeric conformation formed from the EGFR kinase having a mutation of L834R, V924R, V745M or combination of any two or three of L834R, V924R and V745M, such as combination of L834R with V924R.

In another embodiment of the sixth aspect, the EGFR kinase is associated with oncogenesis, preferably prostate cancer, and more preferably metastatic and/or castration-resistant prostate cancer.

In another embodiment of the sixth aspect, the conformation of the EGFR kinase is associated with oncogenesis, preferably prostate cancer, and more preferably metastatic and/or castration-resistant prostate cancer.

In another embodiment of the sixth aspect, the screening is conducted by the following steps: purified EGFR or the cells expressing EGFR is labeled with the theranostic probe, and then the candidate inhibitors are screened by their ability of competing off the theranostic probe from purified EGFR or the cells expressing EGFR.

In the seventh aspect, the present application provides use of the theranostic probe as defined in the first aspect for enriching the cells expressing EGFR.

In an embodiment of the seventh aspect, the EGFR expressed by the cells is a wild type.

In another embodiment of the seventh aspect, the EGFR expressed by the cells has a mutation of L834R, V924R, V745M or combination of any two or three of L834R, V924R and V745M, such as combination of L834R with V924R.

In another embodiment of the seventh aspect, the EGFR is present in a dimeric conformation. In another embodiment of the seventh aspect, the EGFR is present in a dimeric conformation formed from the EGFR of a wild type. In another embodiment of the seventh aspect, the EGFR is present in a dimeric conformation formed from the EGFR having a mutation of L834R, V924R, V745M or combination of any two or three of L834R, V924R and V745M, such as combination of L834R with V924R.

In another embodiment of the seventh aspect, the EGFR is associated with oncogenesis, preferably prostate cancer, and more preferably metastatic and/or castration-resistant prostate cancer.

In another embodiment of the seventh aspect, the conformation of the EGFR is associated with oncogenesis, preferably prostate cancer, and more preferably metastatic and/or castration-resistant prostate cancer.

In another embodiment of the seventh aspect, the enrichment is conducted by the following steps:

labeling the cells expressing EGFR with the theranostic probe as defined in the first aspect; and collecting the labeled cells expressing EGFR.

The present application may be embodied in any other forms without departing from the spirit or scope thereof. The present application encompasses any and all combinations of the above aspects and embodiments. It is to be understood that any embodiment may be combined with any other embodiment(s) to describe an additional embodiment. It is also to be understood that an individual element from any embodiment may be combined with any and all other elements from any other embodiment(s) to describe an additional embodiment.

Dose-dependent inhibition of EGFR kinase activity by PDCy3. HEK293T cells transfected with plasmids encoding the EGF receptor were starved in serum free medium for 2 days before they were treated with EGF, PDCy3, or gefitinib. The expression and phosphorylation levels of EGFR were detected by western blotting using antibodies of anti-protein C and 4G10, respectively. (C) Gefitinib could competitively inhibit the binding of PDCy3 to EGFR. EGFR-transfected cells were treated with 1 M PDCy3, 10 nM EGF/1 M PDCy3, or 5 μM gefitinib/10 nM EGF/1 μM PDCy3. The binding of PDCy3 and the expression of EGFR (detected with 528 antibody) were analyzed by FACS. (D) Relative binding of PDCy3 to EGFR-transfected cells. The relative bound PDCy3 equals to the percentage of PDCy3-bound cells times the mean fluorescent intensity of these cells. The bar graphs represented the averages and standard deviations from triplicated experiments.

Figure 3:
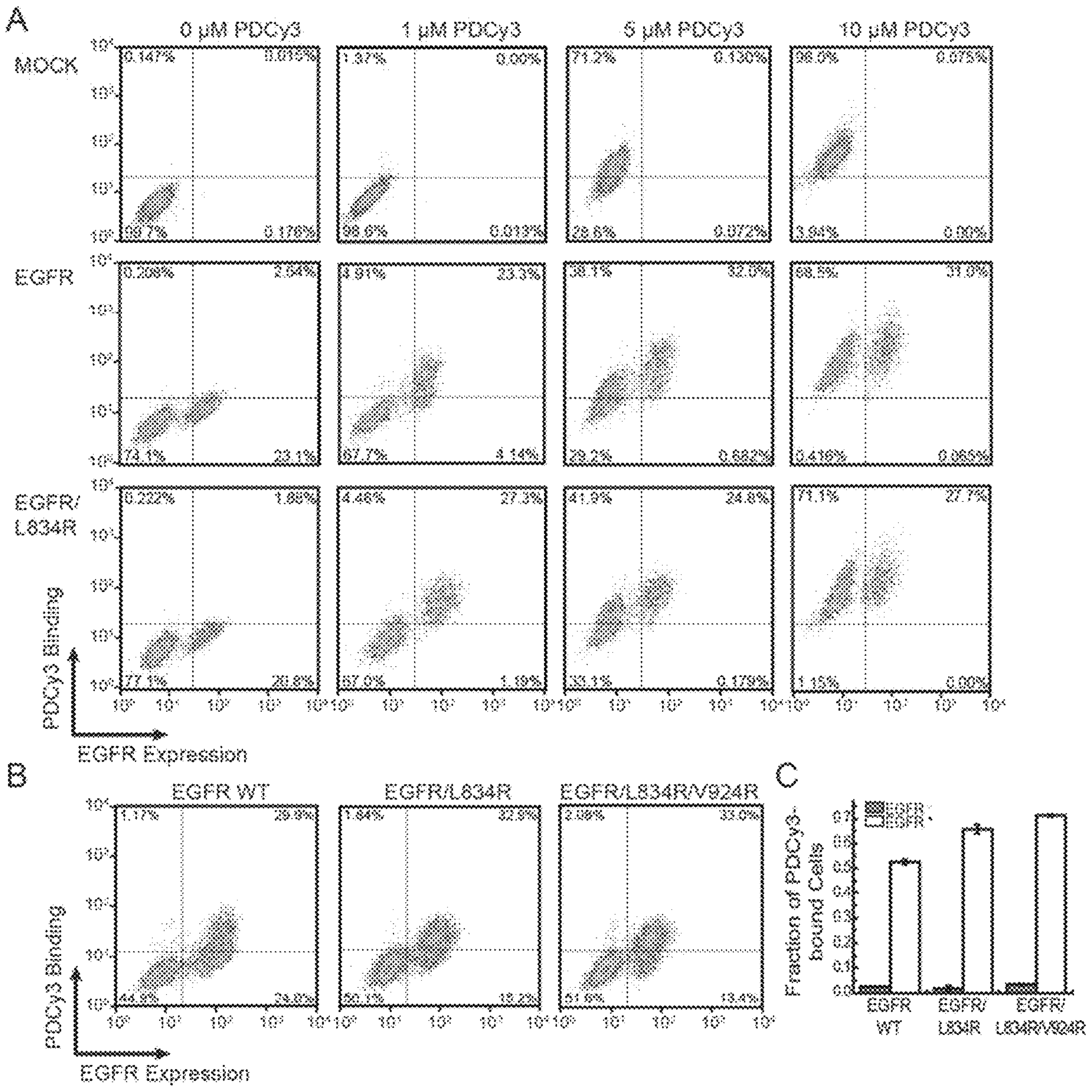

FIG. 3. The binding of PDCy3 to cells was sensitive to EGFR expression and mutation. (A) The binding of PDCy3 to transfected HEK293T cells were compared by flowcytometry under different PDCy3 concentrations. (B) Comparison of PDCy3 binding to cells expressing EGFR wild type or mutants at 1 μM PDCy3 concentration. (C) The fraction of PDCy3-bound cells at 1 μM PDCy3 concentration was used as an index for determining the effects of EGFR mutation on PDCy3 binding. The bar graphs represented the averages and standard deviations from triplicated experiments.

Figure 4:
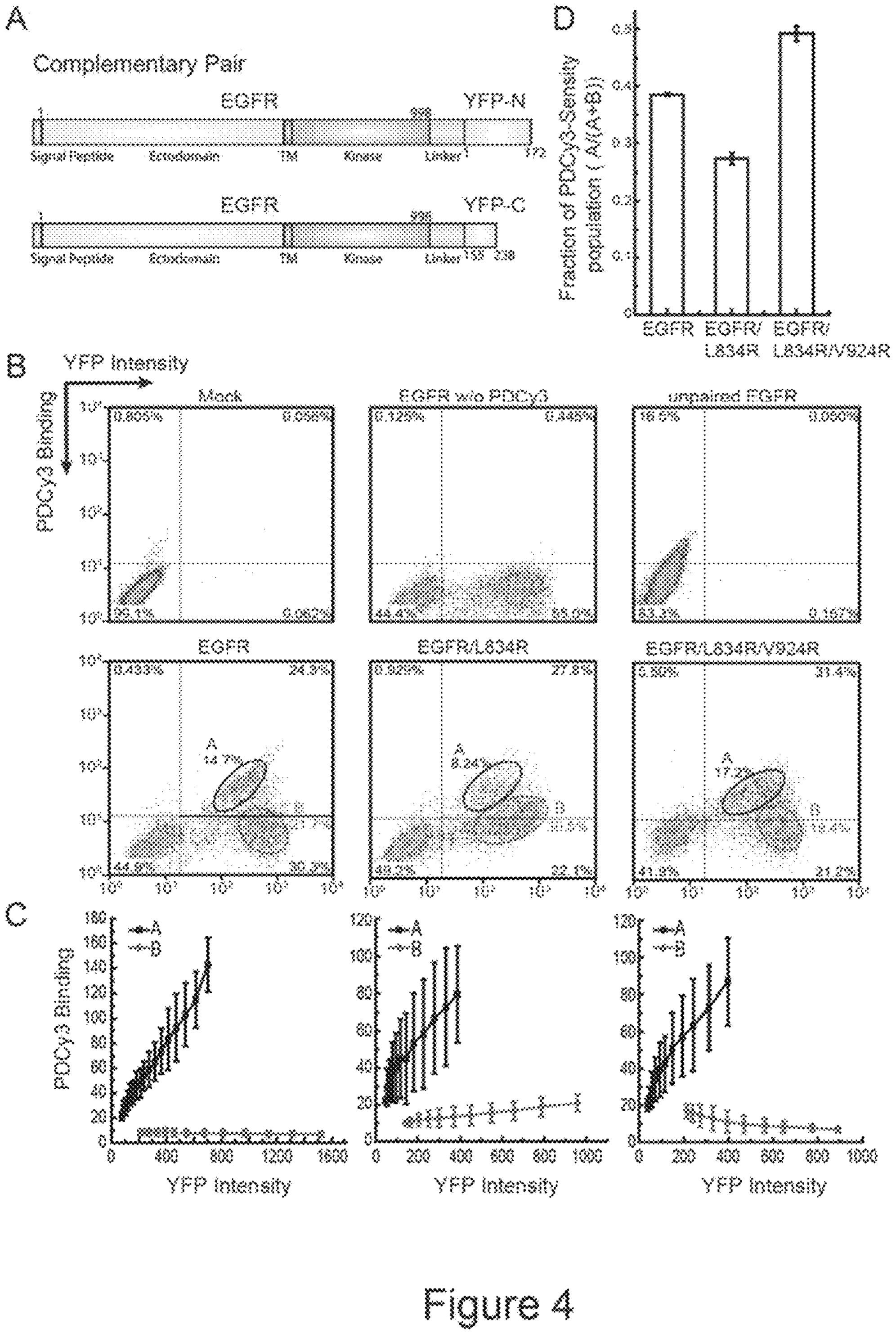

FIG. 4. The effect of EGFR dimerization on PDCy3 sensitivity. (A) A protein complementary pair were designed to express EGFR with attached split-YFP fragments. Refolded YPF structure and restored fluorescence could be achieved upon dimerization of paired receptors on cell surface. (B) The relationship between EGFR dimerization and PDCy3 binding was studied using the designed receptor pair. Each mutation was introduced simultaneously into paired receptors. Two EGFR dimerized populations with different sensitivities to PDCy3 (noted as population A and B) could be identified by FACS at 1 μM PDCy3 concentration. (C) For each population, YFP positive cells were divided into evenly distributed sub-populations based on their YFP intensities. The mean fluorescent intensities and corresponding standard deviations from PDCy3 binding to the cells were plotted as a function of YFP intensities of these cells, which correlated with the expression levels of EGFR dimers. (D) The effects of EGFR oncogenic mutation and asymmetric dimerization on PDCy3 binding. The fractions of PDCy3-sensitive populations were calculated from triplicated experiments.

Figure 5:
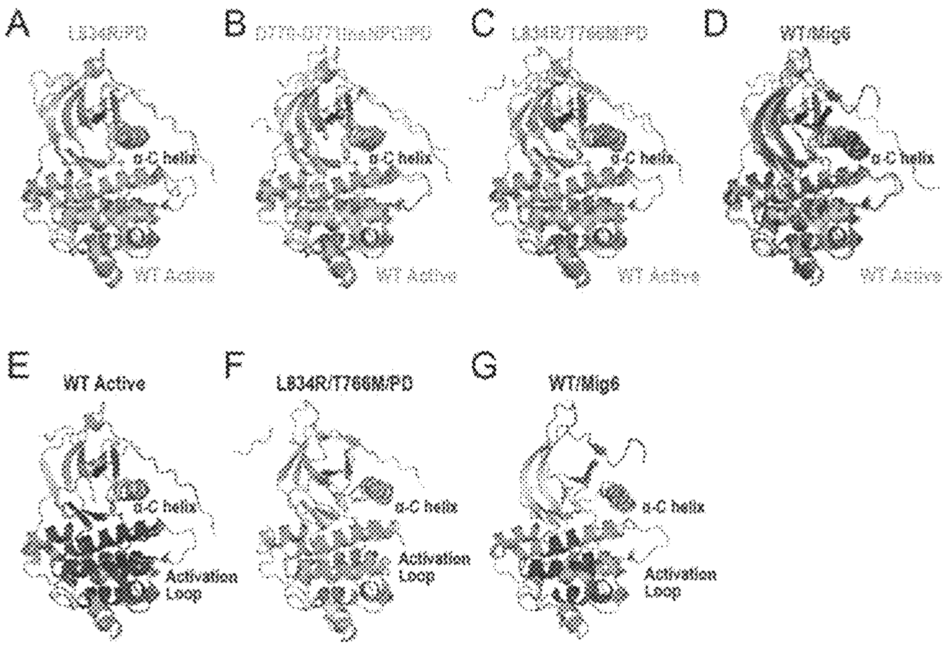

FIG. 5. Comparison of PD168393 bound EGFR kinase structures. (A-C) Crystal structures of PD168393 bound EGFR kinases were compared with the structure of the wild type kinase adopted in active conformation (shown in light blue cartoon, pdb 2GS6). (A) EGFR L834R kinase mutant in complex with PD168393 (green, pdb 4LQM); (B) EGFR D770-D771InsNPG kinase mutant complexed with PD168393 (yellow, pdb 4LRM); (C) EGFR L834R/T766M kinase mutant complexed with PD168393 (light pink, pdb 4LL0). (D) Comparison of the active EGFR kinase structure with the structure of EGFR kinase complexed with Mig6, which has an intrinsically disordered α-C helix (hot pink, pdb 2RF9). (E-G) Comparison of the B-factors of EGFR kinase structures. Representations of the active (E), PD168393-bound L834R/T766M mutant (F), and Mig6-bound (G) EGFR kinase structures were colored according to the B-factors of their Ca atoms. Salt bridge between Lys721 and Glu 736 remains in the structures of the active and PD168393-bound L834R/T766M mutant kinases (E, F), but is broken in the structure of Mig6-bound kinase (G).

Figure 6:
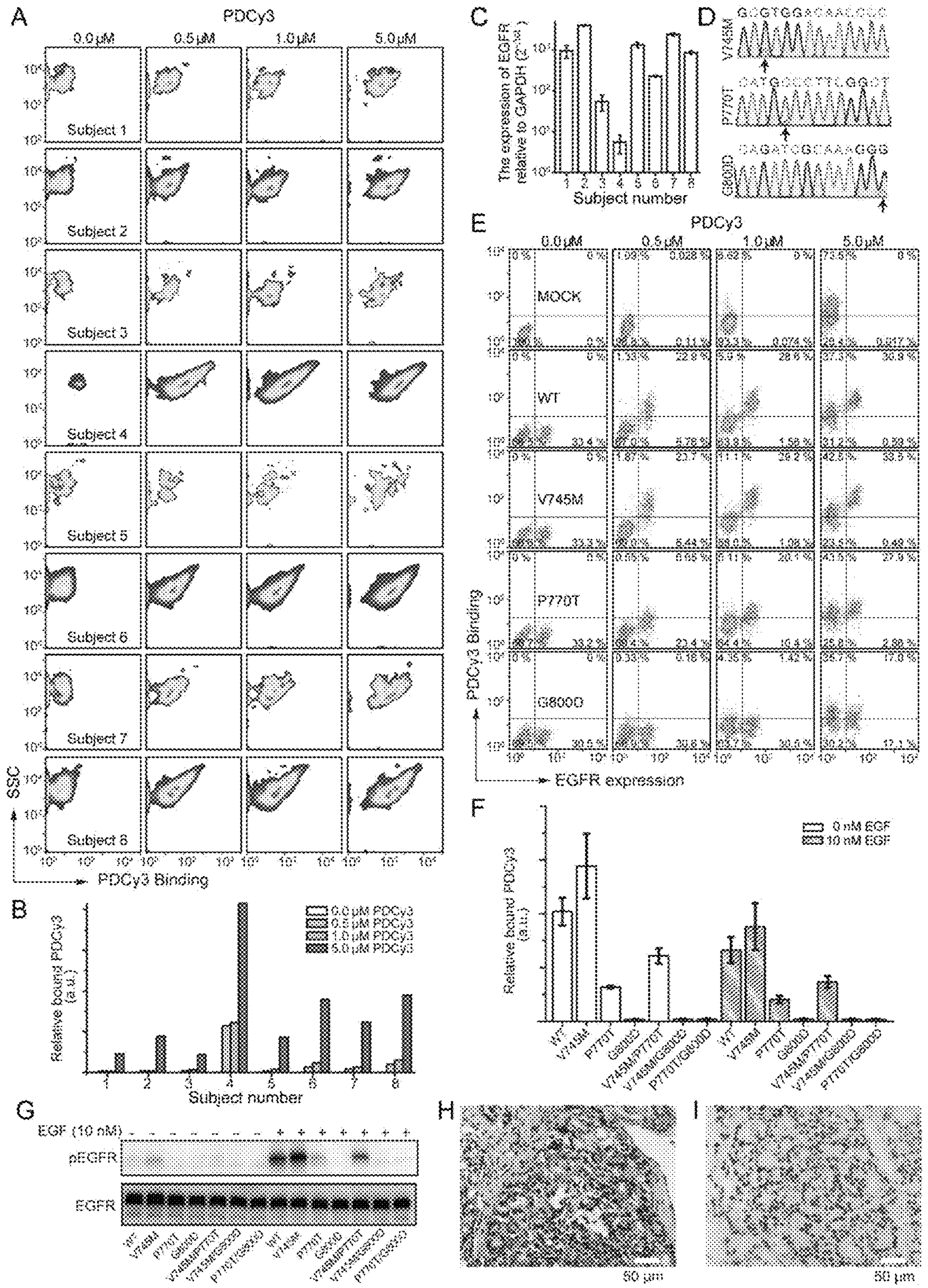

FIG. 6. Chemical stratification of urine samples from cancer patients. (A) The cytometry profiles of PDCy3 binding to the samples from different subjects. The void urine sample from each enrolled subject was stained with PDCy3 under indicated concentrations. The stained samples were analyzed by flowcytometry. (B) Comparison of the relative binding of PDCy3 to the cells collected from different subjects under indicated PDCy3 concentrations. The relative binding of PDCy3 was calculated as the timing of the percentage of PDCy3 positive cells and the mean fluorescent intensity of bound PDCy3. (C) Comparison of the expression levels of EGFR relative to GAPDH in the cells collected from different subjects by RT-qPCR. (D) Three mutations on EGFR kinase domain were detected by forward Sanger sequencing in the sample from subject 4. The cDNA fragment encoding EGFR kinase domain was amplified by 20-cycle PCR using extracted RNA from each sample as the template and a high fidelity polymerase as the enzyme. Mutations on the PCR product from each sample were analyzed by Sanger sequencing. (E) The effects of identified EGFR mutations on PDCy3 binding. 293T cells were transiently transfected with mock, or expression plasmids encoding WT EGFR and its mutants. The binding of PDCy3 to those transfected cells were analyzed by flowcytometry under indicated PDCy3 concentrations. (F) Comparison of the relative binding of PDCy3 to WT EGFR and its mutants. The relative binding of PDCy3 to the cells transfected with WT EGFR and its mutants were compared under 0.5 μM PDCy3 concentration in the presence or absence of 10 nM EGF. The relative binding of PDCy3 was determined as described. The bar graphs represented the means and the standard deviations from triplicated experiments. (G) The effects of identified mutations on EGFR kinase activity. The phosphorylation and expression levels of EGFR were detected by western blotting using 4G10 and anti-protein C antibodies, respectively. (H) HE staining of the biopsy specimen from subject 4. (I) Immunohistochemically staining of expressed androgen receptor on the specimen from subject 4. Androgen receptor was detected with antibody ab74272.

Figure 7:
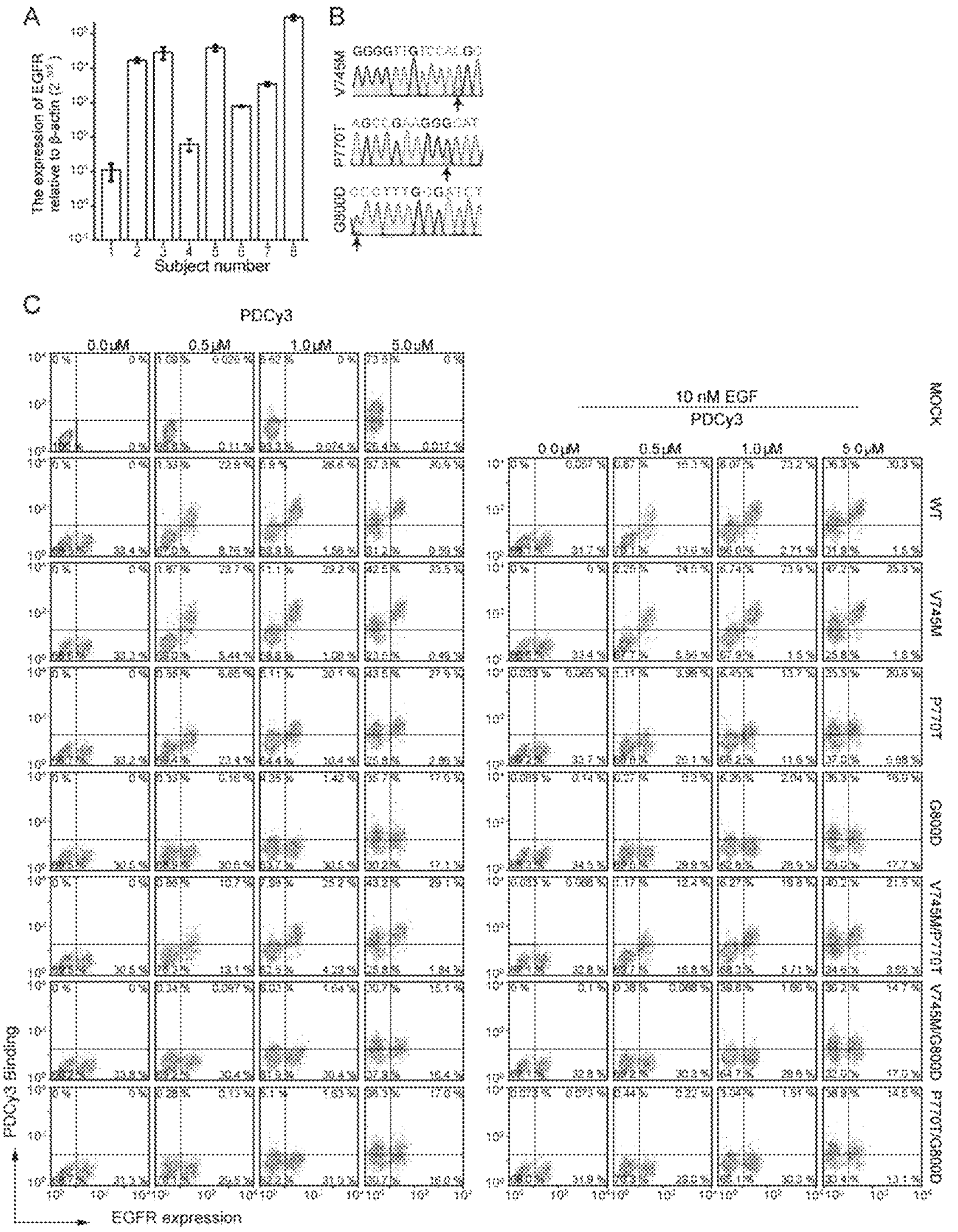

FIG. 7. The expression and mutation of EGFR in cancer patients. (A) Comparison of the expression levels of EGFR relative to R-actin in the cells collected from different subjects by Q-PCR. (B) Mutations on EGFR kinase domain were detected by reverse Sanger sequencing in the sample from subject 4. (C) The effects of identified EGFR mutations on PDCy3 binding. 293T cells were transiently transfected with mock, or expression plasmids encoding WT EGFR and its mutants. The binding of PDCy3 to those transfected cells were analyzed by flowcytometry under indicated PDCy3 concentrations in the presence and absence of 10 nM EGF.

Figure 8:
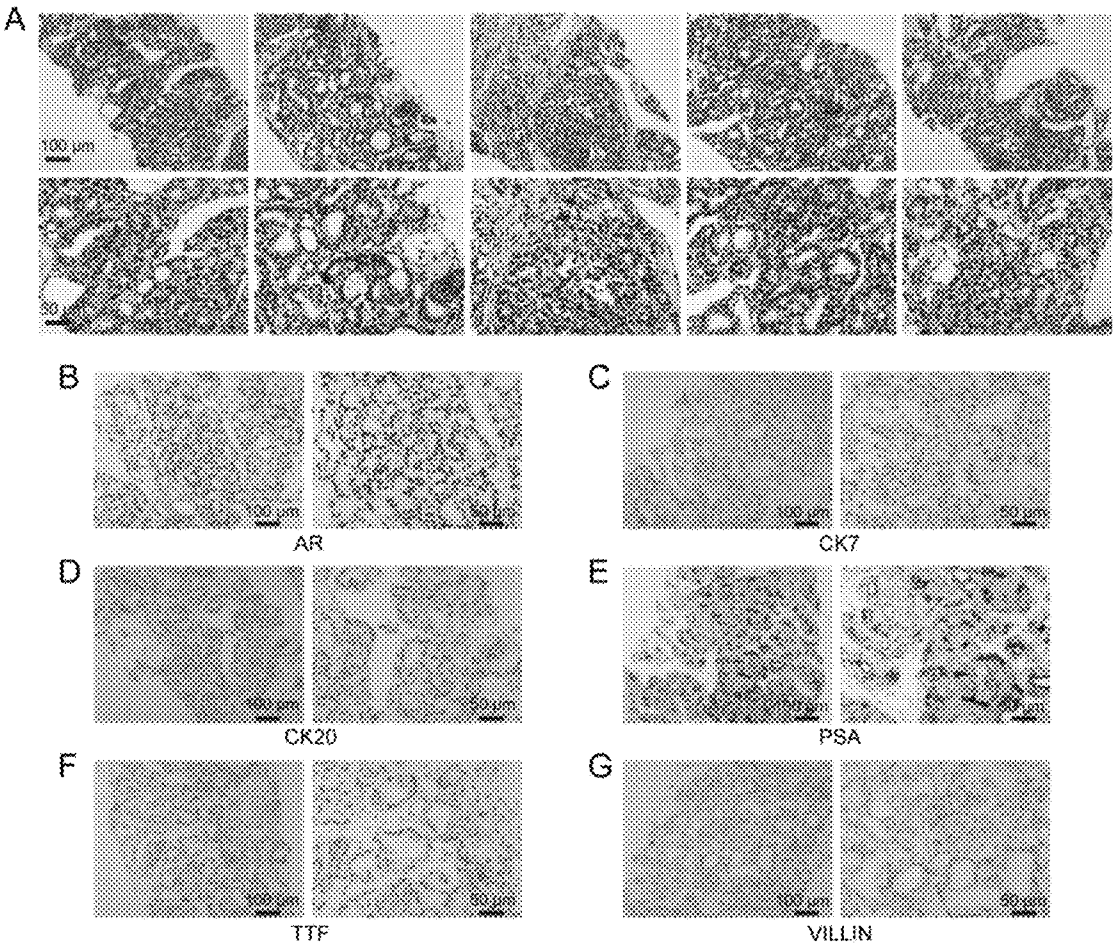

FIG. 8. Tissue biopsy of the specimen from subject 4. (A) HE staining of the specimen. (B, C, D, E, F, G) Immunohistochemically staining of expressed androgen receptor (B), CK7 (C), CK20 (D), PSA (E), TTF (F), and Villin (G) on the specimen.

EXAMPLES

Example 1. Preparation of the Probes

General Procedures $^{1}H$ NMR spectra were recorded on Bruker AVIII 400.

LCMS measurement was run on Agilent 1200 HPLC/6100 SQ System using the follow condition: Mobile Phase: A: Water (10 mM $NH_4HCO_3$), B: MeCN. Gradient: 5% B increase to 95% B within 1.3 min. Flow Rate: 1.8 mL/min. The column used for the chromatography is a 4.6×50 mm XBridge C18 column (3.5 μm particles). Detection methods are diode array (DAD) and evaporative light scattering (ELSD) detection as well as positive/negative electrospray ionization.

Synthesis Scheme
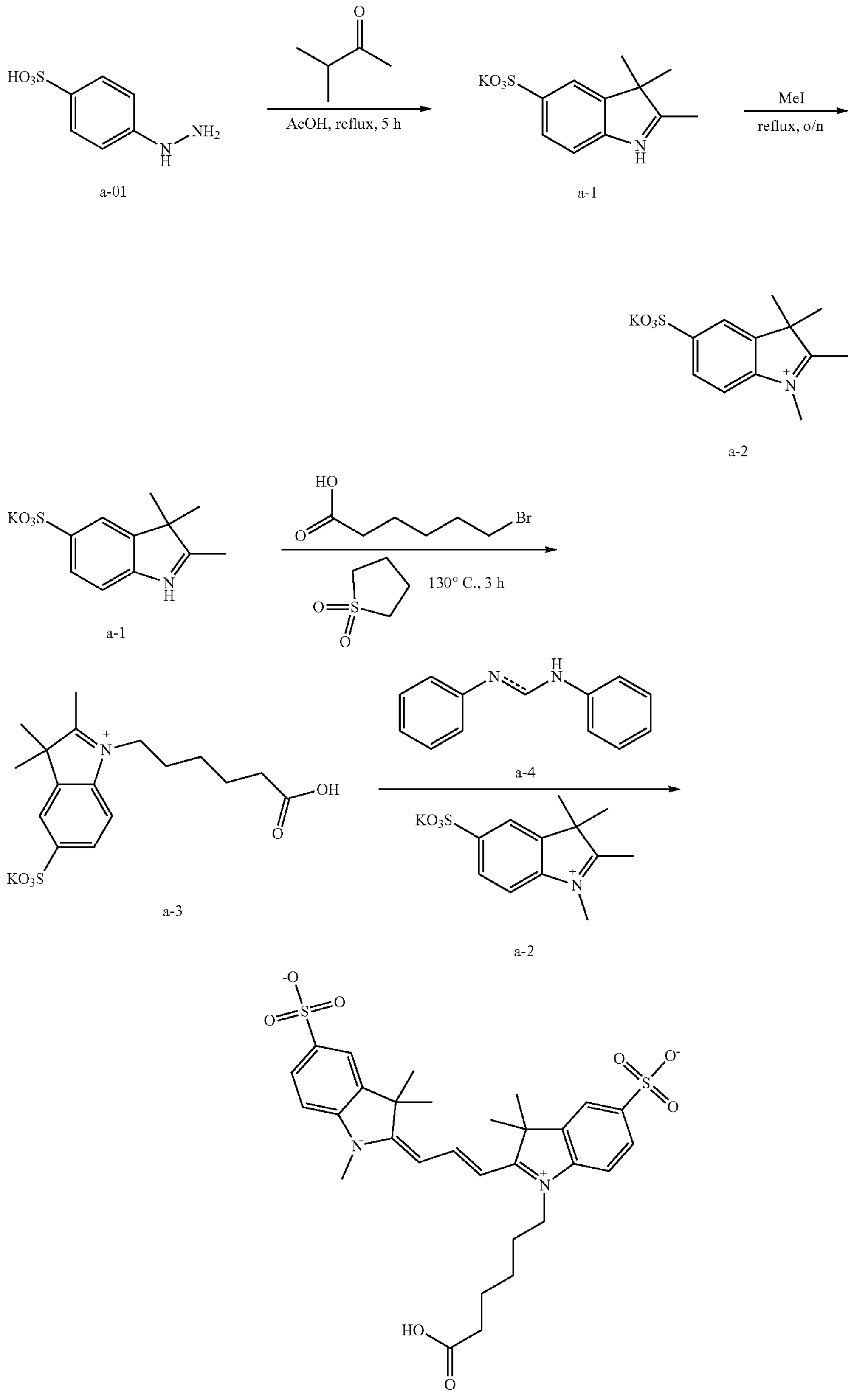
a-01
a-1
a-2
a-1
a-3
a-4
a-2
compound A

-continued
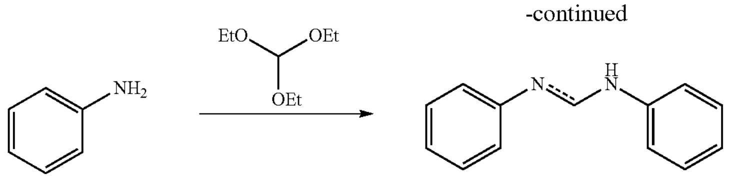
a-02 a-4
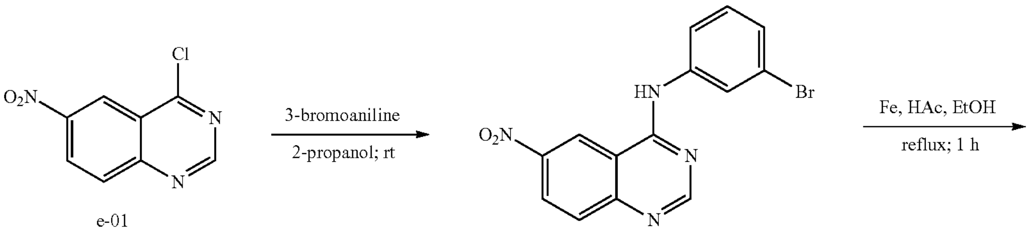
e-01 e-1
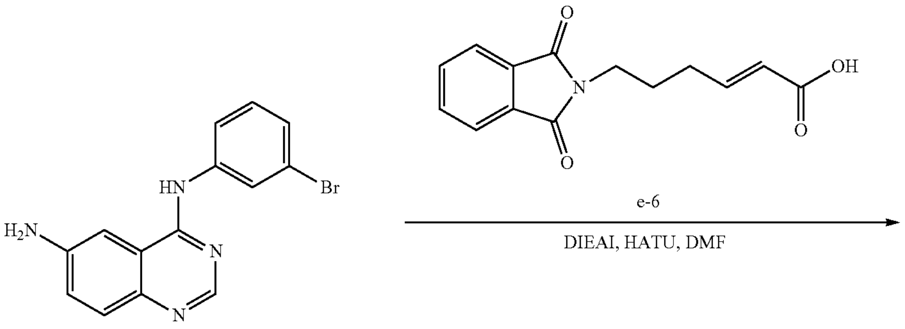
e-6
e-2
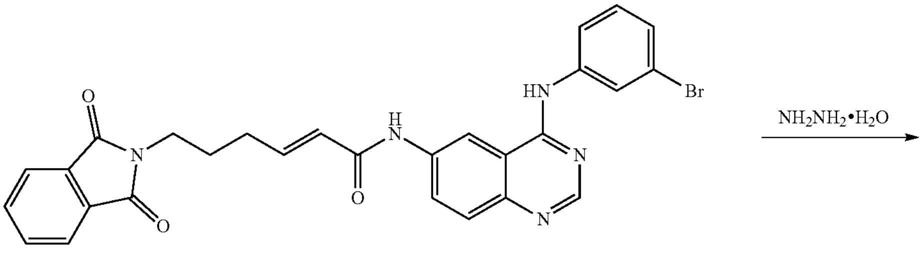
e-7
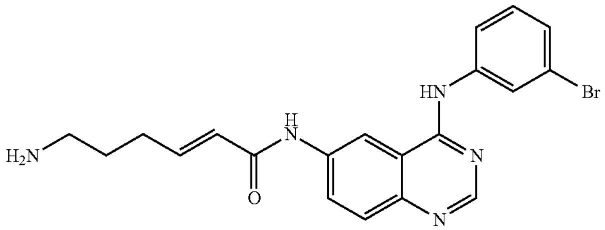
compound E
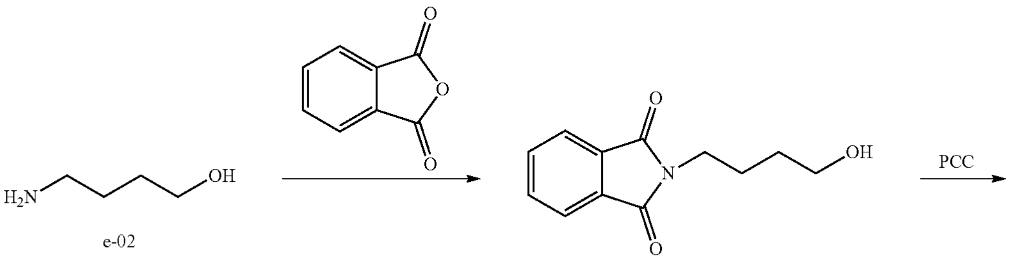
e-02 e-3

-continued
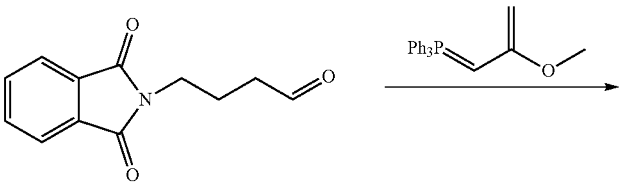
e-4
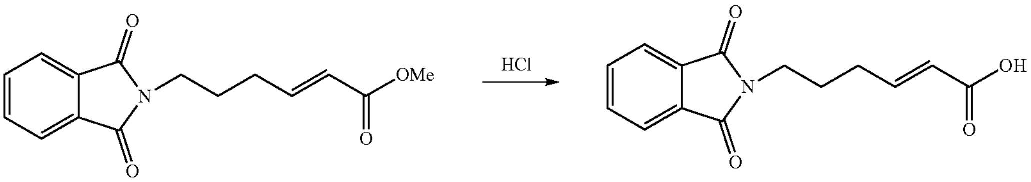
e-5 e-6
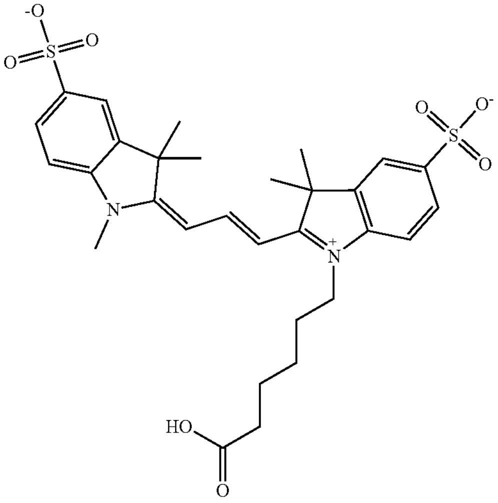
compound A
+
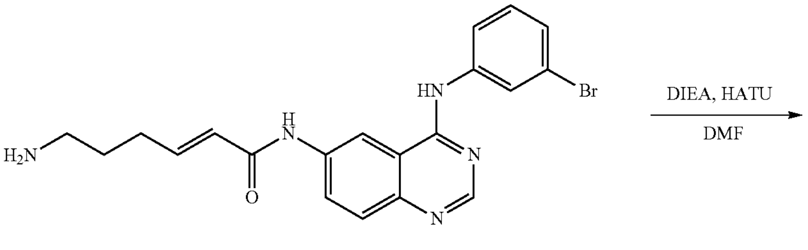
compound E -continued

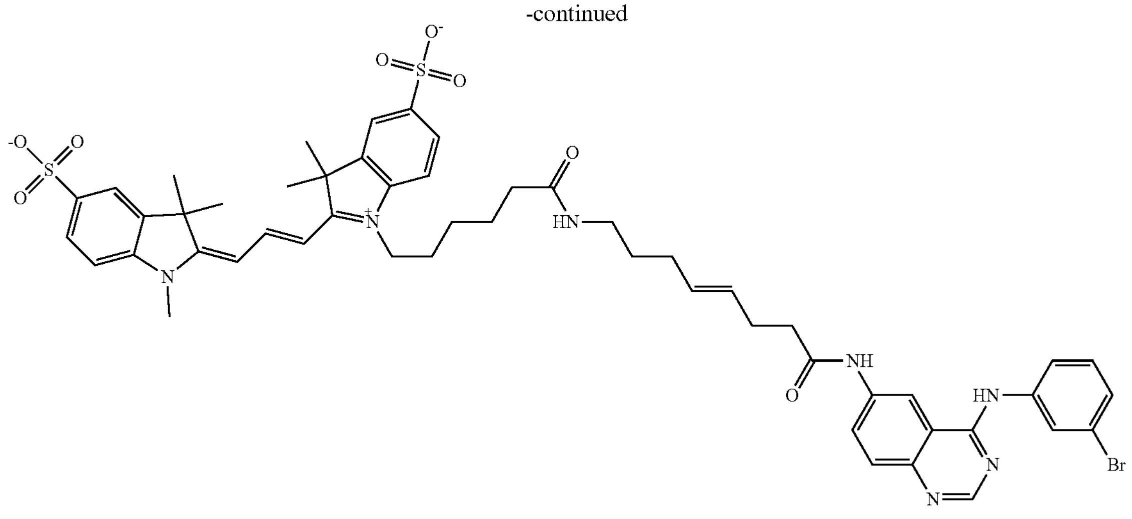

compound 2

In the following syntheses, a counterion, if necessary, is present and is a sodium ion, unless indicated otherwise.

1. Synthesis of Compound α-1:

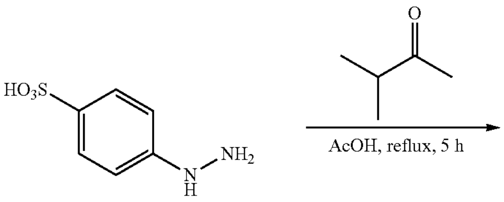

a-01

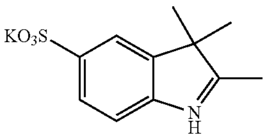

a-1

α-01 (5.0 g, 26.56 mmol) was dissolved in AcOH (30 mL), and 3-methylbutan-2-one (4.58 g, 53.13 mmol) was added. The mixture was heated to reflux for 5 hours. And then the solution was cooled to room temperature. Then a saturated solution of $CH_3COOK$ in 2-propanol was added, solid was observed at this process, and filtered to obtain α-1 5.5 g (74%) as a yellow solid.

LCMS: Mobile Phase: A: Water (10 mM $NH_4HCO_3$), B: MeCN. Gradient: 5% B increase to 95% B within 1.3 min. Flow Rate: 1.8 mL/min. The column used for the chromatography is a 4.6x50 mm XBridge C18 column (3.5 μm particles). Detection methods are diode array (DAD) and evaporative light scattering (ELSD) detection as well as positive/negative electrospray ionization.

LC/MS m/z 240.0 $[M+H]^+$. RT=1.17 min.

2. Synthesis of Compound α-2:

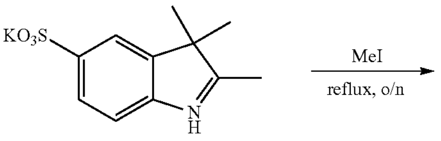

a-1

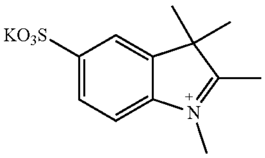

a-2

2.2 g of 2,3,3-trimethylindoleninium-5-sulfonate (α-1) were suspended in 30 mL of methyl iodide. The reaction mixture was heated to boiling for 25 hours in a sealed tube. After the mixture was cooled, excess methyl iodide was decanted, and the residue was suspended in 50 mL of acetone. The solution was filtered to obtain α-2 2.48 g (98% purity) as a pink solid.

LCMS: Mobile Phase: A: Water (10 mM $NH_4HCO_3$), B: MeCN. Gradient: 5% B increase to 95% B within 1.3 min. Flow Rate: 1.8 mL/min. The column used for the chromatography is a 4.6x50 mm XBridge C18 column (3.5 μm particles). Detection methods are diode array (DAD) and evaporative light scattering (ELSD) detection as well as positive/negative electrospray ionization.

LC/MS m/z 254.0 $[M+H]^+$. RT=1.34 min.

3. Synthesis of Compound α-3:

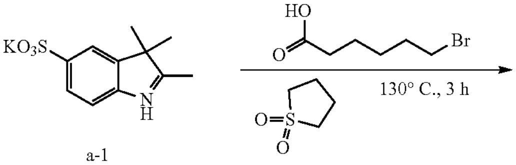

a-1

-continued

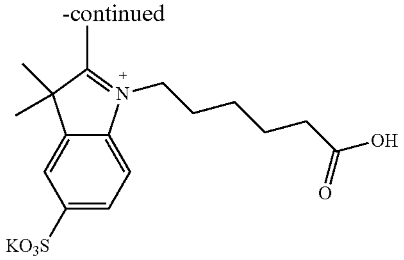

a-3

α-1 (2.77 g, 10 mmol) and 6-bromo-n-hexanoic acid (2.34 g, 12 mmol) were dissolved in sulfolane (2.5 mL), and heated at 130° C. for 3 hours. The reaction mixture was allowed to cool to ambient temperature, then DCM was added to the residue, and the resulting solid was filtered and dried under reduced pressure to obtain a pink solid.

LCMS: Mobile Phase: A: Water (10 mM $NH_4HCO_3$), B: MeCN. Gradient: 5% B increase to 95% B within 1.3 min. Flow Rate: 1.8 mL/min. The column used for the chromatography is a 4.6×50 mm XBridge C18 column (3.5 μm particles). Detection methods are diode array (DAD) and evaporative light scattering (ELSD) detection as well as positive/negative electrospray ionization.

LC/MS m/z 353.0 $[M+H]^+$. RT=1.19 min.

4. Synthesis of Compound α-4:

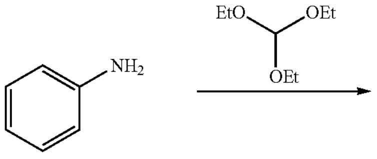

a-02

-continued

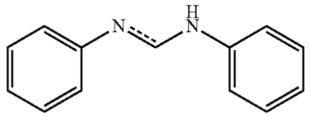

a-4

β-CD (25.77 g, 21.48 mmol) was dissolved in $H_2O$ (200 under warn condition till clear solution obtained, then it was allowed to cool to room temperature. To this clear solution, amine (20.0 g, 214.75 mmol) was added dropwise with stirring followed by dropwise addition of triethylorthoformate (15.91 g, 107.38 mmol), and the reaction was allowed to stir at room temperature overnight. After completion of the reaction (monitored by TLC), the reaction mass was extracted with ethyl acetate. The combined organic layer on evaporation leads to crude product which further purified by simple recrystallization in hexane-ethyl acetate giving pure products α-4 as a white solid.

LCMS: Mobile Phase: A: Water (10 mM $NH_4HCO_3$), B: MeCN. Gradient: 5% B increase to 95% B within 1.3 min. Flow Rate: 1.8 mL/min. The column used for the chromatography is a 4.6×50 mm XBridge C18 column (3.5 μm particles). Detection methods are diode array (DAD) and evaporative light scattering (ELSD) detection as well as positive/negative electrospray ionization.

LC/MS m/z 196.0 $[M+H]^+$. RT=1.83 min.

5. Synthesis of Compound Compound A:

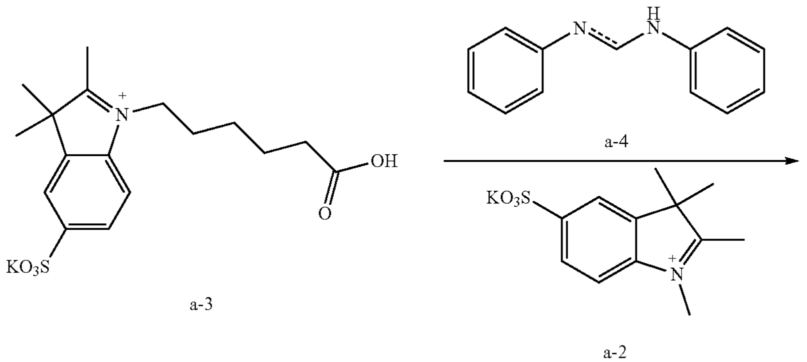

-continued

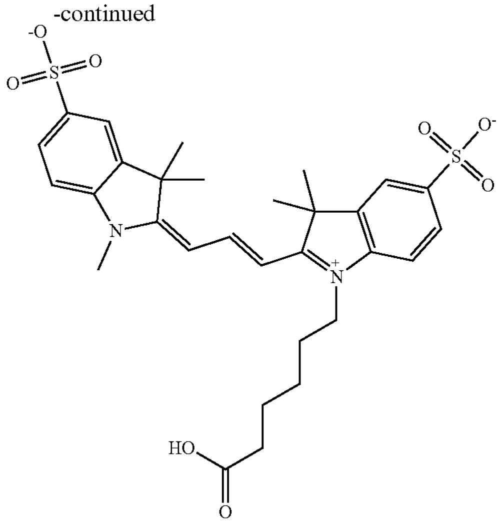

compound A

A solution of α-3 (2.95 g, 7.52 mmol) and α-4 (1.77 g, 9.03 mmol) in acetic acid (4.5 mL) and acetic anhydride (4.5 mL) was heated at 120° C. for 4 hours. The completion of the reaction was monitored by absorption spectra in methanol. Then added α-2 (2.2 g, 7.52 mmol) and more acetic anhydride (4.5 mL) and pyridine (4.5 mL). The mixture is heated for 30 min until the anyl intermediate disappears (monitored by absorption spectra). The reaction mixture was cooled and poured into ethyl acetate (50 mL). The crude product is collected by centrifugation and washed with ethyl acetate twice. Preparative HPLC purification gives Compound A (260 mg) as a dark purple solid.

LCMS: Mobile Phase: A: Water (10 mM $NH_4HCO_3$), B: MeCN. Gradient: 5% B increase to 95% B within 1.3 min. Flow Rate: 1.8 mL/min. The column used for the chromatography is a 4.6×50 mm XBridge C18 column (3.5 μm particles). Detection methods are diode array (DAD) and evaporative light scattering (ELSD) detection as well as positive/negative electrospray ionization.

LC/MS m/z 617.0 [M+H]). RT=1.15 min.

$^1$H NMR (400 MHz, $D_2O$) δ 8.43-8.36 (t, J=26.8 Hz, 1H), 7.77-7.76 (d, J=1.6 Hz, 2H), 7.71-7.68 (m, J=12 Hz, 2H), 7.24-7.19 (m, J=20.8 Hz, 211), 6.27-6.20 (m, J=29.6 Hz, 2H), 3.97-3.93 (t, J=14.4 Hz, 2H), 3.54-3.47 (d, J=28 Hz, 3H), 2.08-2.05 (t, J=14.8 Hz, 2H), 1.72-1.66 (m, J=22.4 Hz, 2H), 1.61 (s, 12H), 1.53-1.46 (t, J=29.6 Hz, 2H), 1.33-1.28 (m, J=23.6 Hz, 2H).

6. Synthesis of Compound e-1:

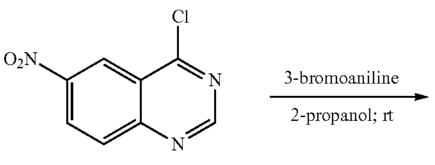

e-01

-continued

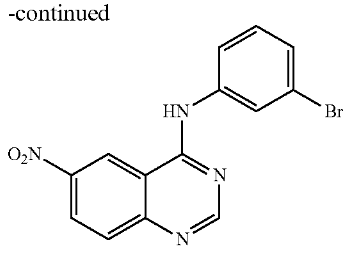

e-1

To a solution of e-01 (2 g, 9.5 mmol) in 2-propanol was added 3-bromoaniline (1 mL, 9.5 mmol) and the resulting mixture was allowed to stir at room temperature overnight under argon. The precipitate that formed was filtered and washed with water and ether, after which it was dried under vacuum to give 6-nitro-4-(3-bromophenylamino)quinazoline (e-1) (72%) as a yellow solid.

LCMS: Mobile Phase: A: Water (10 mM $NH_4HCO_3$), B: MeCN. Gradient: 5% B increase to 95% B within 1.3 min. Flow Rate: 1.8 mL/min. The column used for the chromatography is a 4.6×50 mm XBridge C18 column (3.5 μm particles). Detection methods are diode array (DAD) and evaporative light scattering (ELSD) detection as well as positive/negative electrospray ionization.

LC/MS m/z 344.0 $[M+H]^+$. RT=1.90 min.

7. Synthesis of Compound e-2:

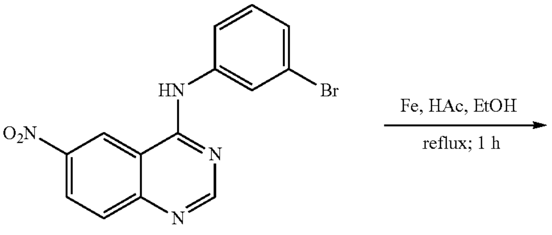

e-1

-continued

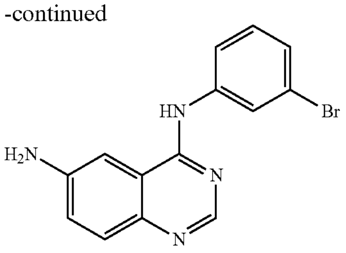

e-2

To a solution of the isolated e-1 (1.0 g, 2.80 mmol) in aqueous ethanol (1:2, 58 mL) and acetic acid (2.8 mL) was added Fe (1.95 g. 34.77 mmol), and the resulting cloudy mixture was kept under reflux for 1 hour. The reaction was cooled to room temperature, alkalinized with concentrated ammonia, and extracted by DCM. The organic layer was dried by $Na_2SO_4$ and concentrated under reduced pressure to obtain the target compound e-2 as a yellow solid.

LCMS: Mobile Phase: A: Water (0.1% TFA) B: ACN (0.1% TFA) Gradient: 5% B increase to 95% B within 1.5 min. Flow Rate: 1.5 mL/min. The column used for the chromatography is a 4.6×50 mm XBridge C18 column (3.5 μm particles). Detection methods are diode array (DAD) and evaporative light scattering (ELSD) detection as well as positive/negative electrospray ionization.

LC/MS m/z 316.0 $[M+H]^+$. RT=1.00 min.

8. Synthesis of Compound e-3:

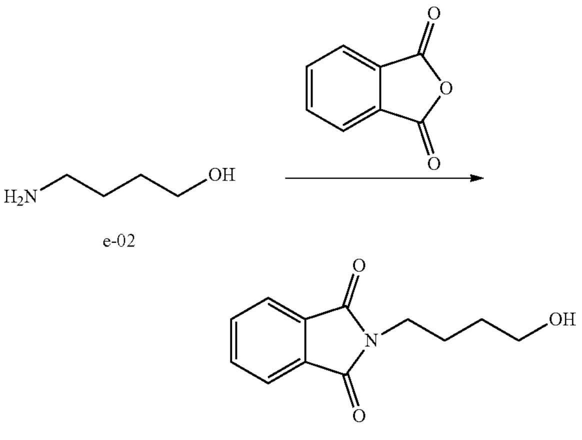

e-02 e-3

A mixture of 4-amino-1-butanol (SM-1) (5 g, 56.09 mmol) and phthalic anhydride (8.30 g, 56.09 mmol) in toluene (150 mL) was heated to reflux under Dean-Stark conditions for 3 h. After cooling, removal of solvent in vacuo produced the crude product which was purified by flash column chromatography eluting with PE/EA providing a colorless oil, which upon standing became a colorless crystalline solid 12.4 g (97%).

LCMS: Mobile Phase: A: Water (10 mM $NH_4HCO_3$), B: MeCN. Gradient: 5% B increase to 95% B within 1.3 min. Flow Rate: 1.8 mL/min. The column used for the chromatography is a 4.6×50 mm XBridge C18 column (3.5 μm particles). Detection methods are diode array (DAD) and evaporative light scattering (ELSD) detection as well as positive/negative electrospray ionization.

LC/MS m/z 219.0 $[M+H]^+$. RT=1.52 min.

9. Synthesis of Compound e-4:

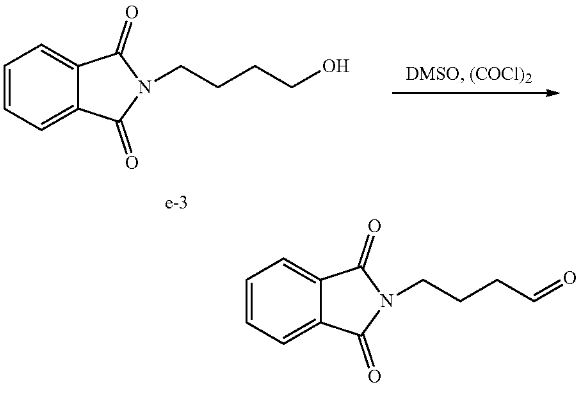

e-3 e-4

A solution of dimethyl sulfoxide (6.45 ml, 22.81 mmol) in dichloromethane was added dropwise to a solution of oxalyl chloride (5.79 g, 45.61 mmol) in dichloromethane at −78° C., followed by adding dropwise thereto a solution of 2-(4-hydroxybutyl)-1H-isoindole-1,3(2H)-dione (e-3) (5.0 g, 22.81 mmol) in dichloromethane.

After stirring for 20 minutes, a solution of triethylamine (9.23 g, 91.22 mmol) in dichloromethane was added thereto and the reaction temperature was raised to 0° C., followed by stirring for another 30 minutes. After completion of the reaction, a saturated aqueous sodium chloride solution was added thereto, followed by extraction with ethyl acetate. The organic layer was washed with water and a saturated aqueous sodium chloride solution and then dried over anhydrous sodium sulfate. The solvent was distilled off under reduced pressure to obtain the title compound (6.0 g, 82% purity).

LCMS: Mobile Phase: A: Water (0.1% TFA) B: ACN (0.1% TFA) Gradient: 5% B increase to 95% B within 1.5 min. Flow Rate: 1.5 mL/min. The column used for the chromatography is a 4.6×50 mm XBridge C18 column (3.5 μm particles). Detection methods are diode array (DAD) and evaporative light scattering (ELSD) detection as well as positive/negative electrospray ionization.

LC/MS m/z 217.0 [M+H]. RT=1.05 min.

10. Synthesis of Compound e-5:

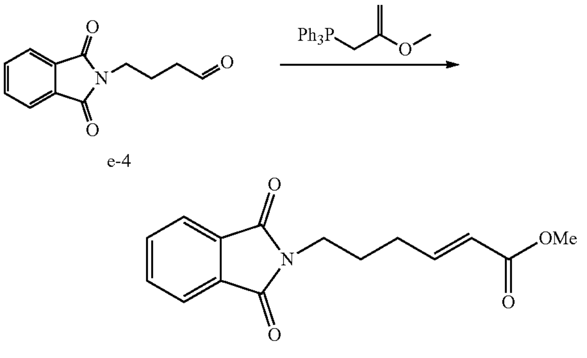

e-4 e-5

4-Phthalimidobutanal (1.0 g, 4.60 mmol) was dissolved in CH2Cl2 (10 mL) and treated with methyl (triphenylphosphoranylidene)-acetate (1.53 g, 4.60 mmol) in CH2Cl2 (10 mL). After 1 h, the mixture was concentrated, poured onto a silica gel column, packed in and eluted with PE/EA, and obtained the product as a white solid (79%).

11. Synthesis of Compound e-6:
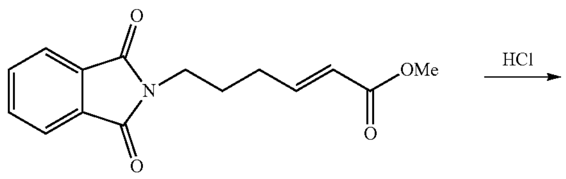
e-5
-continued
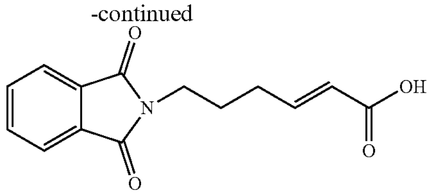
e-6
A solution of e-5 (0.9 g, 3.29 mmol) and 4 N HCl (10 mL) solution in dioxane was refluxed for 4 h. The solution was cooled to RT and the solvent was removed. The residue was submitted to column chromatography ($SiO_2$, DCM to EtOAc) to afford the title compound as a white solid.
12. Synthesis of Compound e-7:
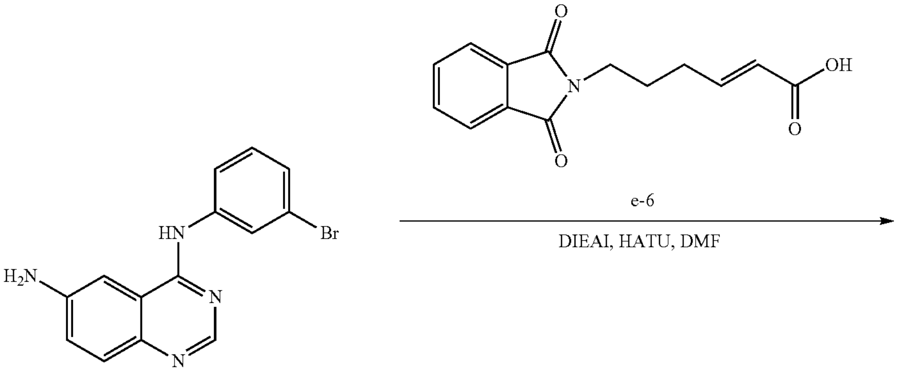
e-6
e-2
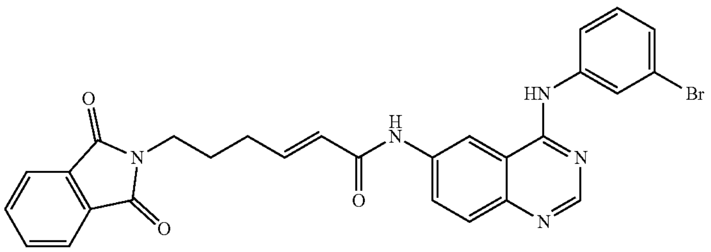
e-7 e-2 (1.0 g, 3.17 mmol), e-1 (0.55 g, 2.11 mmol) and HATU (0.63 g, 1.66 mmol) were dissolved in DCM (10 mL) and DMF (1 mL). Then added N-ethyl diisopropylamine (0.041 mg, 3.17 mmol), and the mixture was stirred at room temperature for 2 hours. Then extracted by DCM, the organic layer was dried by $Na_2SO_4$ and concentrated to get the crude product and purified by silica gel column (eluent: DCM/MeOH).

LCMS: Mobile Phase: A: Water (10 mM $NH_4HCO_3$), B: MeCN. Gradient: 5% B increase to 95% B within 1.3 min. Flow Rate: 1.8 mL/min. The column used for the chromatography is a 4.6×50 mm XBridge C18 column (3.5 μm particles). Detection methods are diode array (DAD) and evaporative light scattering (ELSD) detection as well as positive/negative electrospray ionization.

LC/MS m/z 557.0 $[M+H]^+$. RT=1.88 min.

13. Synthesis of Compound E:

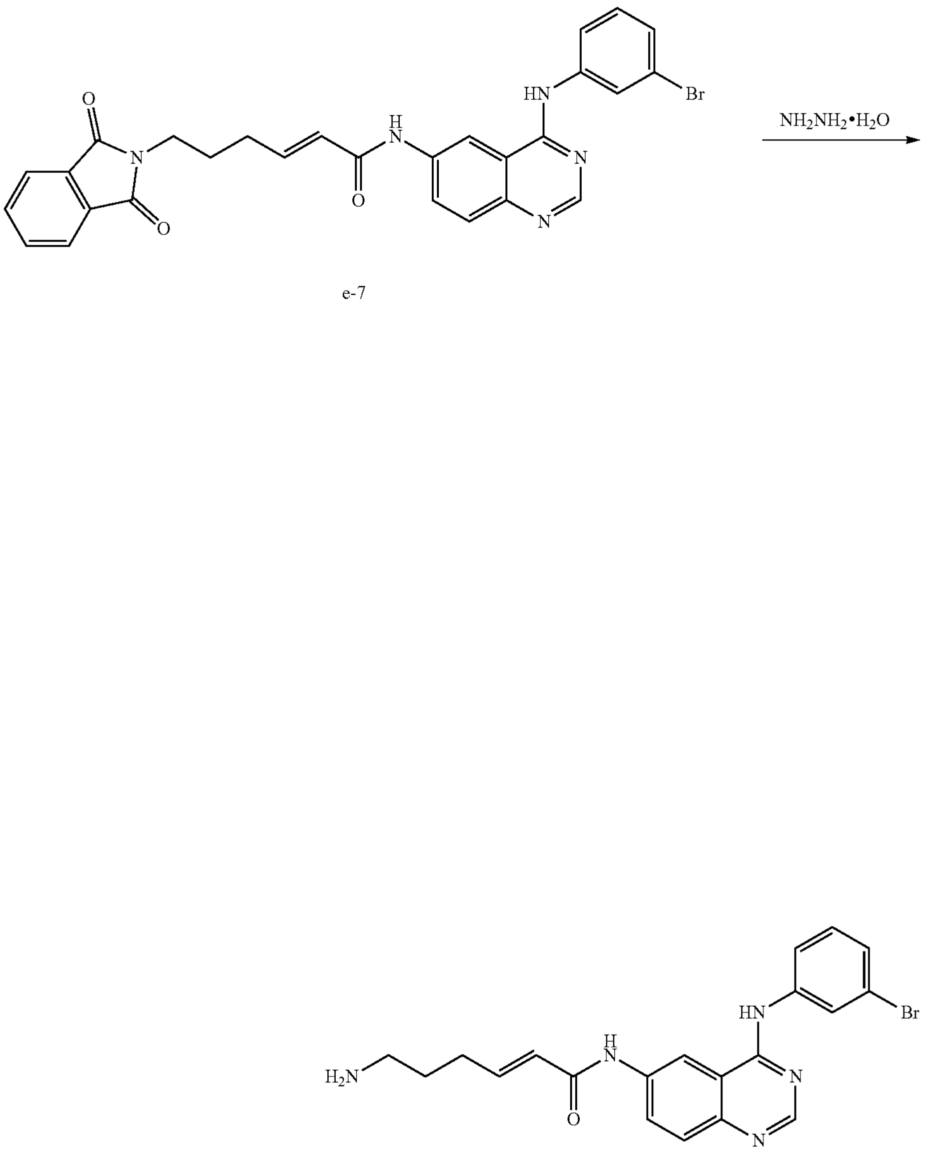

e-7 compound E e-7 (1.4 g, 2.52 mmol) was dissolved in EtOH (60 mL) and CHCl3 (20 mL), and the mixture was heated to 80° C. NH2NH2·H2O (0.7 mL) was added to the solution, and the mixture was heated at 80° C. for 1 hour. Then it was allowed to cool to room temperature, and the precipate was removed by filtration and washed by EtOH. The filtrate was concentrated to get the crude product. Preparative HPLC purification gives Compound E (600 mg) as a yellow solid.

LCMS: Mobile Phase: A: Water (10 mM $NH_4HCO_3$), B: MeCN. Gradient: 5% B increase to 95% B within 1.3 min. Flow Rate: 1.8 mL/min. The column used for the chromatography is a 4.6×50 mm XBridge C18 column (3.5 μm particles). Detection methods are diode array (DAD) and evaporative light scattering (ELSD) detection as well as positive/negative electrospray ionization.

LC/MS m/z 425.0 $[M+H]^+$. RT=1.60 min.

14. Synthesis of PDCy3 (Compound 2):

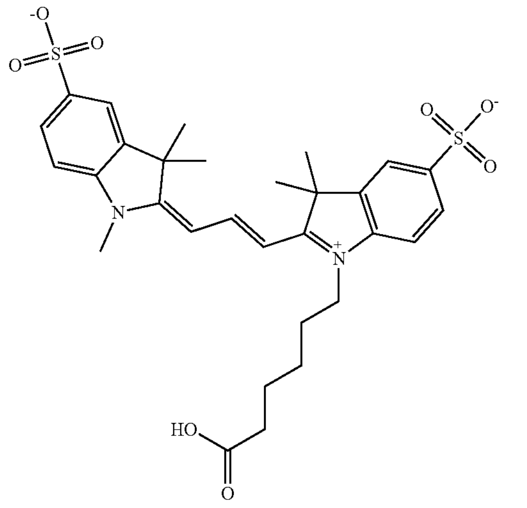

compound A

+

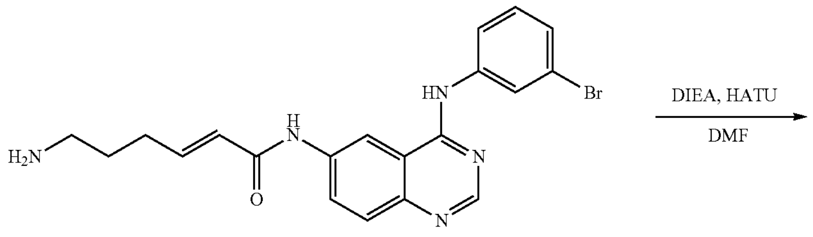

compound E

-continued

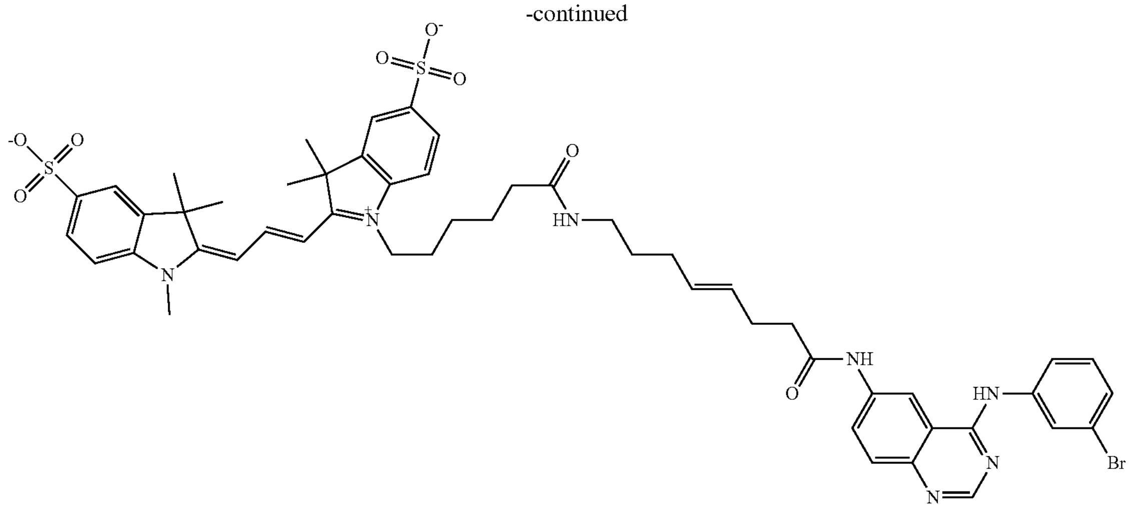

Compound 2

Compound A (50 mg, 0.081 mmol), compound E (51 mg, 0.12 mmol) and HATU (33 mg, 0.088 mmol) were dissolved in DCM (2 mL). Then added N-ethyl diisopropylamine (20.9 mg, 0.16 mmol), and the mixture was stirred at room temperature for 2 hours. Then purified by Pre-HPLC to get compound 2 (40 mg) as a pink solid.

LCMS: Mobile Phase: A: Water (10 mM $NH_4HCO_3$), B: MeCN. Gradient: 5% B increase to 95% B within 1.3 min. Flow Rate: 1.8 mL/min. The column used for the chromatography is a 4.6x50 mm XBridge C18 column (3.5 μm particles). Detection methods are diode array (DAD) and evaporative light scattering (ELSD) detection as well as positive/negative electrospray ionization.

Compound 2:

1-(6-((E)-6-(4-(3-bromophenylamino)quinazolin-6-ylamino)-6-oxohex-4-enylamino)-6-oxohexyl)-3,3-dimethyl-2-((1E,3E)-3-(1,3,3-trimethyl-5-sulfonatoindolin-2-ylidene)prop-1-enyl)-3H-indolium-5-sulfonate Chemical Formula: $C_{50}H_{53}BrN_7O_8S_2^-$ MW: 1024.03/mol Appearance: Pink solid LC/MS m/z 1024.0 $[M+H]^+$, $[M+H]^+/2$. RT=1.46 min.

$^1H$ NMR (400 MHz, DMSO) δ 10.37 (s, 1H), 8.83 (d, 1H), 8.68 (s, 1H), 8.33 (t, 1H), 8.13 (s, 1H), 8.02-8.01 (s, J=2 Hz, 1H), 7.80-7.99 (d, J=2 Hz, 1H), 7.82-7.79 (m, J=11.2 Hz, 4H), 7.72-7.66 (m, J=21.6 Hz, 2H), 7.44-7.37 (m, J=28 Hz, 4H), 7.22 (s, 1H), 7.09 (s, 1H), 7.96 (s, 1H), 6.51-6.46 (d, J=17.6 Hz, 2H), 4.30 (s, 1H), 4.12 (s, 2H), 3.65-3.63 (d, J=7.6 Hz, 3H), 2.75-2.71 (t, J=17.6 Hz, 1H), 2.33 (s, 1H), 2.21-2.15 (m, J=24.4 Hz, 2H), 1.90-1.85 (m, J=21.2 Hz, 2H), 1.75-1.73 (d, J=8 Hz, 2H), 1.68 (s, 12H), 1.67-1.65 (d, J=10 Hz, 1H), 1.5 (s, 2H).

Example 2. Biological Assays

Materials and Methods

Materials. The plasmids encoding human EGFR (1-988) and split YFP fragments were obtained from Addgene (#11011, #27097, and #22010) as gifts from Dr. Timothy A. Springer and Dr. Chang-Deng Hu. Gefitinib from MedChem Express (NJ, USA) and recombinant human EGF from Sino Biological Inc (China) were reconstituted and stored as recommended by the manufactures. Restriction enzymes and Gibson assembly kit were purchased from NEB (MA, USA); DNA polymerase was from Vazyme (China); anti-protein C antibody was from Genscript (China); and anti-phoshotyrosine antibody 4G10 was from Merck Millipore (USA).

The synthesis of PDCy3. The details for the synthesis of PDCy3 were described in the supplementary methods. The synthesized material was characterized by 1H NMR spectra recorded on Bruker AVIII 400 and LCMS measurement running on Agilent 1200 HPLC/6100 SQ System. For LCMS experiment, the mobile phase A was water (10 mM $NH_4HCO_3$), and mobile phase B was MeCN. The material was eluted from a 4.6x50 mm XBridge C18 column (3.5 μm particles) by a linear gradient of 5% B to 95% B within 1.3 minutes. The flow rate was 1.8 mL/min. Detection methods were diode array (DAD), evaporative light scattering (ELSD), and positive/negative electrospray ionization.

Inhibition of the EGF receptor kinase activity. HEK 293T cells cultured in 24-well plates were transfected as described. Transfected cells were starved in EX-Cell 293 Serum-Free Medium (SIGMA) supplemented with 6 mM Glutamine for 44 hours before treatment with EGF, inhibitor, or the probe. Treated cells were lysed by mixing with 40 μl/well lysis buffer (50 mM Tris, pH 7.5, 150 mM NaCl, 1% TritonX-100, 1% sodium deoxycholate, 0.1% SDS, 10 mM EDTA, 1 mM $Na_3VO_4$, 2 mM PMSF). The lysates were then cleared by centrifugation at 13,200 μg for 20 min. The supernatants were mixed with 6xSDS sample buffer, and were subjected to SDS-PAGE and Western blotting analysis. The expression and phosphorylation levels of EGFR were detected by 4G10 and anti-Protein C antibodies, respectively, in western blotting.

Cell sorting. Following starvation in EX-Cell 293 Serum-Free Medium for 44 hours, transfected cells were treated with gefitinib, PDCy3, or EGF for 4 hours at 37° C. Then, the cells were washed twice with 500 μl/well ice-cold PBS, and were re-suspended in 400 μl/well PBS. The final cell density was estimated to be $5\times10^5$~$1\times10^6$ cells/ml. To detect EGFR expression, 3 μd anti-EGFR 528 antibody (santa cruz biotechnology inc, USA) at 200 μg/ml concentration was added to each well of re-suspended cells. After 30-minute incubation on ice, cells were washed twice with 500 μl/well PBS, and were re-suspended in 400 1 PBS. Then, 0.3 μl FITC-labelled secondary antibody at a concentration of 2 mg/ml was added to each sample. After incubation on ice for 30 minutes, cells were washed three times with PBS, resuspended in 400 μl/well PBS, and analyzed by flowcytometry using a BD FACS Calibur machine.

Protein complementary assay. For protein complementary assay, we designed two complementary constructs: one encoding human EGFR(1-998) fused with a split YFP-N(1-172) fragment, and the other encoding hEGFR(1-998) linked to a split YFP-C(155-238) fragment. Kinase mutations were introduced on both constructs to make a complementary pair. All the constructs were verified by sequencing. The paired constructs encoding the same receptor were co-transfected into HEK 293T cells. Transfected cells were starved in EX-Cell 293 Serum-Free Medium for 44 hours before treatment with 1 μM PDCy3 for additional 4 hours. The dimerization of the EGF receptors and the binding of dimerized receptors to PDCy3 were analyzed by flowcytometry.

Results

The Fluorescent Probe could Competitively Inhibit the Kinase Activity of EGFR.

Figure 1:
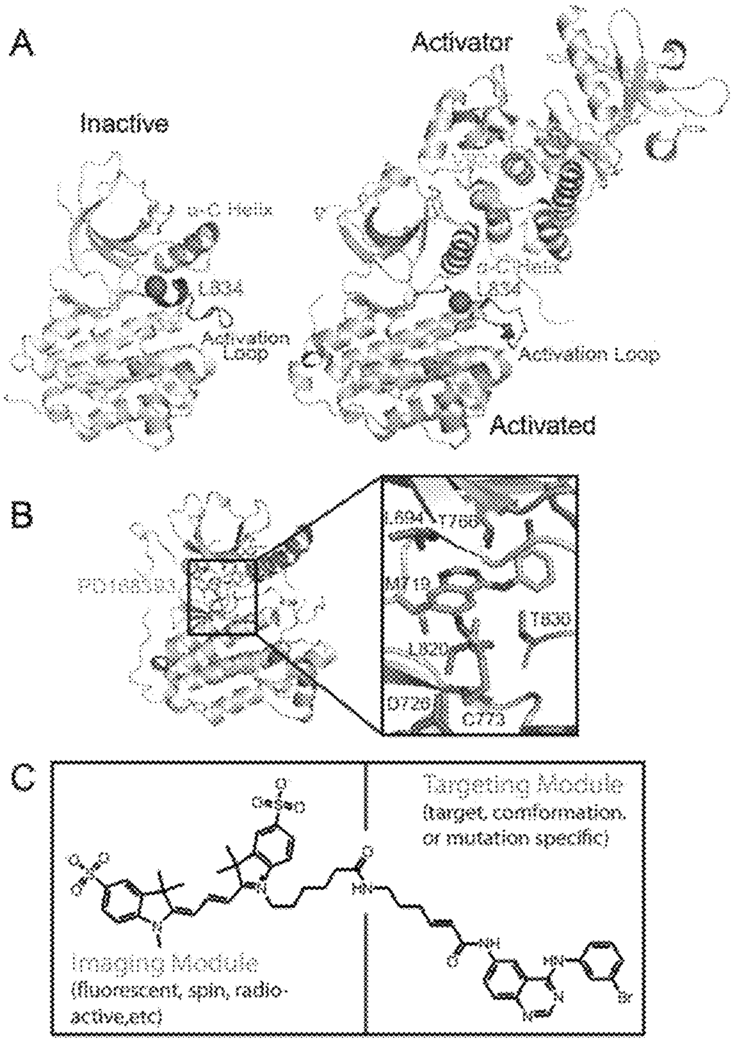
FIG. 1. Modular design of EGFR-targeting probes. A) EGFR kinase domain adopted in inactive (left, PDB 2GS7) [15] and active (right, PDB 2GS6)[15] conformations were shown in cartoon. In the inactive conformation, the kinase α-C helix (cyan) swings out, and the activation loop (blue) forms a short helix to stabilize the positioning of the α-C helix. The oncogenic mutation L834R, located at the activation loop, was highlighted in red. In the active conformation, two EGFR kinases form a specific, asymmetric dimer, in which one acts as an activator (light blue) to stabilize the other (magenta) in activated state. Mutation of V924R (green) could disrupt the asymmetric dimerization[15]. B) The overall structure (left) and details (right) of PD168393-bound EGFR kinase (PDB 4LL0)[18]. PD168393 (gold) binds to the active site of EGFR kinase (light blue). The acrylamide group of PD168393 is pointing to the outside of the kinase. The residues interact with the inhibitor were shown in blue sticks. C) The modular design of a theranostic probe. Acyl chains were extended from PD168393 (targeting module) and Cy3 (imaging module), respectively, and were linked together by an amide bond. Both modules are exchangeable for different applications.
Figure 2:
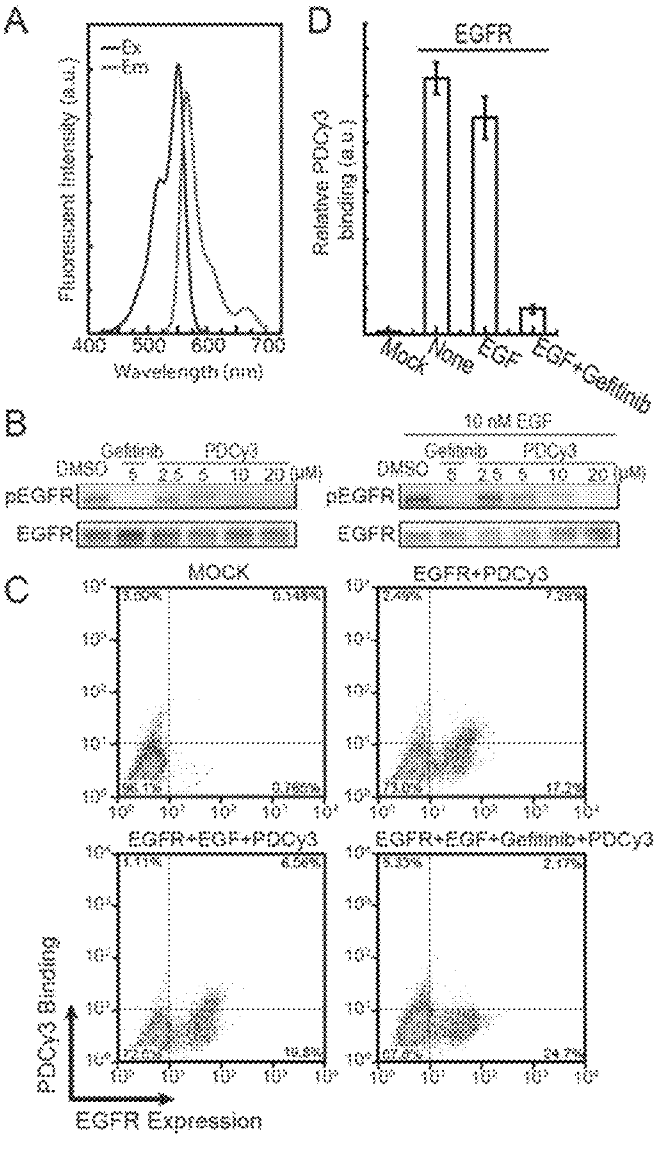
FIG. 2. PDCy3 could specifically inhibit the EGFR kinase activity. (A) The fluorescent spectrum of PDCy3 in DMSO. Black, excitation spectrum; red, emission spectrum. (B)

The functions of each module of the probe were analyzed individually. Overall, the fluorescent spectrum of our synthesized probe is quite similar to the spectrum of Cy3, except an additional minor peak at 674 nm shown in the emission spectrum (FIG. 2A). This additional minor peak in the emission spectrum could extend the detectable range of the PDCy3 probe to visible red color region in imaging applications, such as FRET experiments.

Then, we analyzed the inhibitory effects of the PDCy3 probe on EGFR kinase activity (FIG. 2B). In the assay, EGFR-transfected HEK293T cells were treated with the PDCy3 probe at different concentrations for 10 minutes in the presence and absence of 10 nM EGF. The expression and phosphorylation levels of the EGF receptor were detected and analyzed by western blotting. As shown in the FIG. 2B, the probe could inhibit the kinase activity of EGFR in a dose dependent manner. Complete inhibition of EGFR kinase activity was achieved at the probe concentration of 20 μM. In comparison, the kinase activity of EGFR was completely inhibited by 5 μM gefitinib under the same condition (FIG. 2B).

Using gefitinib as a competitor[19], we confirmed the inhibitory specificity of the PDCy3 probe on EGFR kinase activity (FIG. 2C). EGFR- or mock transfected cells were labeled with EGFR-specific antibody 528 and the probe PDCy3 simultaneously in the presence and absence of 5 μM gefitinib. The binding abilities of the PDCy3 probe to EGFR-expressed cells were compared by flowcytometry under different conditions. Treatment with 10 nM EGF did not enhance the binding of the PDCy3 probe to EGFR-expressed cells (FIG. 2C). However, in the presence of EGF, addition of 5 μM gefitinib reduces the population of EGFR-expressed, PDCy3 positive cells from 45.4% to 5.3% (FIG. 2C). These results suggested that the PDCy3 probe could competitively inhibit the kinase activity of EGFR and specifically bind the receptor on transfected cells. From another point of view, this experiment also demonstrated the utility of this PDCy3 probe in screening of EGFR inhibitors by competition.

PDCy3 Probe was Sensitive to EGFR Expression and Oncogenic Mutation.

To extend the application of PDCy3 probe in a diagnosis-related setting, we optimized the labelling conditions so that the cells with over-expressed EGFR could be more specifically labelled with the probe. We compared the efficiencies in labelling EGFR over-expressed cells versus those non-over-expressed cells under different PDCy3 concentrations (FIG. 3A). We found that transfected EGFR-positive cells could be specifically labelled by PDCy3 under 1 μM concentration. Under this condition, over 84.9% EGFR positive cells could be labeled by this probe. In comparison, 6.7% EGFR negative cells and 1.4% mock transfected cells were labelled by PDCy3 probe at the same condition. However, when the concentration of PDCy3 was increased to 5 M or higher, mock transfected cells or transfected, EGFR-negative cells were getting to be labelled non-specifically.

As the PDCy3 probe was derived from PD168393, which is compatible with active and inactive conformations of EGFR kinase and is able to promote EGFR dimerization on the cell surface in the absence of EGF[20, 21], we studied whether this probe would be more sensitive to EGFR activating mutation associated with oncogenesis or to EGFR kinase asymmetric dimerization, which is required for kinase allosteric activation[15] (FIG. 3B). Introduction of L834R mutation, which could destabilize the inactive conformation of EGFR kinase[22], increased the population of PDCy3-bound, EGFR positive cells from 52.4% to 65.9% (FIG. 3B, 3C). Disruption of the asymmetric kinase dimer by introduction of V924R mutation did not impair the binding of PDCy3 to transfected EGFR positive cells, but rather enhance the binding of PDCy3 to those cells by 8% (FIG. 3B, 3C).

To further investigate how EGFR kinase dimerization affects PDCy3 binding, we did a protein complementary assay. In the assay, split YFP fragments were individually fused to the C-terminus of the full length EGFR, and EGF kinase dimerization was reported by the fluorescence of assembled YPF from co-transfected receptors (FIG. 4A)[2]3. As shown in the FIG. 4B, the cells with co-expressed EGFR dimers could be divided into two populations. In one population, the quantity of bound PDCy3 increased linearly as a function of the expression levels of EGFR dimers (FIG. 4C). But in the other population, the quantity of bound PDCy3 was independent of the expressed EGFR dimers. L858R mutation rendered both dimerized receptor populations to be sensitive to PDCy3 binding (FIG. 4C). However, one population, which is equivalent to its wild type counterpart, is 5 times more sensitive than the other in response to PDCy3 binding. In addition, compared with that of the wild type receptor, the population with the higher sensitivity to PDCy3 decreased from 38.4% to 27.4% (FIG. 4C, 4D). On the other hand, V924R mutation introduced on top of L834R did not block the dimerization of co-transfected receptors (FIG. 4C, 4D). Instead, it changed the cell population with less-sensitivity to PDCy3 to be independent of or resistant to the expressed EGFR dimers. Moreover, V924R mutation promoted the cell population with high-sensitivity to PDCy3 from 27.4% to 49.2% (FIG. 4C, 4D). These results in together indicated that there were two different EGFR dimeric forms on the cell surface: one was highly sensitive to PDCy3 binding, the other was not. As V924R mutation could disrupt the asymmetric kinase dimer[15], the dimer identified with high-sensitivity to PDCy3 should be different from that asymmetric, active dimer.

DISCUSSION

In this report, we proposed our concepts in modular design and development of probes targeting oncogenic receptors. With the dramatically increased cost in new drug development and considerably decreased therapeutic targets identified, re-evaluation of drugs used on the market drew more and more attentions from industry and academia. In our structure-based design, we explore the potentials in re-programing the verified EGFR kinase inhibitor for applications in drug screening, cell sorting, and imaging of protein interactions. The benefits for our modular design include, but not limited to, the exchangeable imaging and targeting modules. The exchangeable imaging module could be used at different biological and/or therapeutic settings with their different imaging properties. On the other hand, the exchangeable targeting module could be used for detection of different targets or different states of a specific target. In our case, PDCy3 was selective for EGFR overexpressing cells and was more sensitive to the oncogenic mutation of L834R. Future studies will address whether this probe could be used in clinical diagnosis and how the EGF receptors are dynamically interacting with each other on the cell surface.

Based on their sensitivities to PDCy3 binding, two different cell populations representing different EGFR dimers were identified on the cell surface. In these two populations, one was highly sensitive to PDCy3 binding, but the other was not. L834R mutation promoted the formation of dimers with weak sensitivity to PDCy3 binding, while V924R mutation stimulated the formation of dimers with high sensitivity to PDCy3. Considering that V924R mutation could disrupt the asymmetric, active EGFR kinase dimer and L834R favors the active conformation of the kinase[15, 24], we believe that the EGFR dimers with weak sensitivity to PDCy3 represent the asymmetric, active kinase dimers. On the other side, we believed that the EGFR dimers with high sensitivity to PDCy3 actually represent another kinase association state. From early structural studies, it had been proposed that EGFR kinase domain were capable of forming both the asymmetric, active dimer and the symmetric, inactive dimer in vitro[15, 16]. Intuitively, it is possible that PDCy3-sensitive dimer was equivalent or related to the symmetric, inactive kinase dimer. However, many evidences argued against that possibility. It had been shown that gefitinib and PD168393, being compatible with both active and inactive confonnations of EGFR kinase, could drive the homo- or hetero-dimerization of unligated EGF receptors on cell surface[20, 25] In contrast, lapatinib and HKI-272, both stabilizing the kinase in inactive conformation, failed to do so[20]. Such disparity had been attributed to the conformational, dynamic nature of the kinase[21, 26] Indeed, intermediate transition states of the EGFR kinase had been identified in molecular dynamic simulation[27, 28]. It is intriguing to note that the available structures of PD168393-bound EGFR kinases varied largely at their N-lobe and α-C helix positioning (r.m.s.d. varies from 1.8 Å to 2.7 Å, when they were superimposed on their C-lobes) (FIG. 5A)[29, 30]. And one of these structures (PDB 4LL0) is more close to the intermediate state identified in molecular dynamic simulation with intrinsically disordered α-C helix (PDB 2RF9) (FIG. 5B)[27]. Nevertheless, we provided a tool for dissecting the EGF receptor dimerization and drug sensitivity. Our results indicated that there were two different dimeric kinase populations existed on cell surface. These two different dimerization states associated with different sensitivities to kinase inhibitors. Identification of such difference in kinase dimerization and drug sensitivity could be informative for the development of next generation therapeutics.

Example 3. Biological Assays

Inspired by these unresolved challenges as stated in the section "Background", we designed modular theranostic probes targeting EGFR kinase in specific conformations associated with oncogenesis, and applied the probe-based cytometry in chemical stratification of prostate cancers. We demonstrated examples of using such a probe in screening inhibitors by competition, in sorting cells with over-expressed or mutated EGFR, and in imaging of EGFR interactions on cell surface. Surprisingly, we found that PD168393, an EGFR kinase inhibitor[50], was more reactive to an intermediate state of the kinase distinguished from that active, asymmetric dimer. Moreover, we analyzed eight urine samples from seven confirmed and one putative prostate cancer patients using the probe-based cytometry. These samples showed distinctive responses to the probe: one was highly sensitive to the probe, but the others were not. EGFR mutations were only detected in the sample with high sensitivity to the probe but not in others with overexpressed wild type (WT) EGFR. Clinical analysis confirmed the subject, whose sample was highly sensitive to the probe, progressed to the castration-resistant, metastatic stage.

Materials and Methods

Materials. The plasmids encoding human EGFR (1-988) and split YFP fragments were obtained from Addgene (#11011, #27097, and #22010) as gifts from Dr. Timothy A. Springer and Dr. Chang-Deng Hu. Gefitinib from MedChem Express (NJ, USA) and recombinant human EGF from Sino Biological Inc (China) were reconstituted and stored as recommended by the manufactures. Restriction enzymes and Gibson assembly kit were purchased from NEB (MA, USA); DNA polymerase was from Vazyme (China); anti-protein C antibody was from Genscript (China); and anti-phosphotyrosine antibody 4G10 was from Merck Millipore (USA). Anti-CK7 (ab181598), anti-CK20 (ab76126), anti-Androgen Receptor (ab74272), anti-VILLIN (ab130751), and anti-TTF-1 (ab72876) antibodies were from Abcam (Cambridge, MA, USA); and anti-PSA (31-1210-00) antibody was from RevMAb Biosciences (San Francisco, CA, USA).

The synthesis of PDCy3. The details for the synthesis of PDCy3 were described above. The synthesized material was characterized by $^1$H NMR spectra recorded on Bruker AVIII 400 and LCMS measurement running on Agilent 1200 HPLC/6100 SQ System. For LCMS experiment, the mobile phase A was water (10 mM $NH_4HCO_3$), and mobile phase B was MeCN. The material was eluted from a 4.6×50 mm XBridge C18 column (3.5 μm particles) by a linear gradient of 5% B to 95% B within 1.3 minutes. The flow rate was 1.8 mL/min. Detection methods were diode array (DAD), evaporative light scattering (ELSD), and positive/negative electrospray ionization.

Inhibition of the EGF receptor kinase activity. HEK 293T cells cultured in 24-well plates were transfected as described[51]. Transfected cells were starved in EX-Cell 293 Serum-Free Medium (SIGMA) supplemented with 6 mM Glutamine for 44 hours before treatment with EGF, inhibitor, or the probe. Treated cells were lysed by mixing with 40 μL/well lysis buffer (50 mM Tris, pH 7.5, 150 mM NaCl, 1% Triton X-100, 1% sodium deoxycholate, 0.1% SDS, 10 mM EDTA, 1 mM $Na_3VO_4$, 2 mM PMSF). The lysates were then cleared by centrifugation at 13,200 μg for 20 min. The supernatants were mixed with SDS sample buffer and subjected to SDS-PAGE and Western blotting analysis. The expression and phosphorylation levels of EGFR were detected by 4G10 and anti-Protein C antibodies, respectively, in western blotting.

Cell sorting. Following starvation in EX-Cell 293 Serum-Free Medium for 44 hours, transfected cells were treated with gefitinib, PDCy3, or EGF for 4 hours at 37° C. Then, the cells were washed twice with 500 μL/well ice-cold PBS, and were re-suspended in 400 μL/well PBS. The final cell density was estimated to be $5\times10^5$~$1\times10^6$ cells/mL. To detect EGFR expression, 3 μL anti-EGFR 528 antibody (Santa Cruz Biotechnology Inc, USA) at 200 μg/mL concentration was added to each well of re-suspended cells. After 30-minute incubation on ice, cells were washed twice with 500 μL/well PBS, and were re-suspended in 400 μL PBS. Then, 0.3 μL FITC-labelled secondary antibody at a concentration of 2 mg/mL was added to each sample. After incubation on ice for 30 minutes, cells were washed three times with PBS, re-suspended in 400 μL/well PBS, and analyzed by floweytometry using a BD FACS Calibur machine.

Protein complementary assay. For protein complementary assay, we designed two complementary constructs: one encoding human EGFR(1-998) was fused with a split YFP-N(1-172) fragment; and the other encoding hEGFR(1-998) was linked to a split YFP-C(155-238) fragment. Kinase mutations were introduced on both constructs to make a complementary pair. All constructs were verified by sequencing. The paired constructs encoding the same receptor were co-transfected into HEK 293T cells. Transfected cells were starved in EX-Cell 293 Serum-Free Medium for 44 hours before treatment with 1 M PDCy3 for additional 4 hours. The dimerization of the EGF receptors and the binding of dimerized receptors to PDCy3 were analyzed by flowcytometry.

Cytometry of urine samples from cancer patients. 10-15 mL void urine sample was collected from each cancer patient. The cells in those samples were collected by centrifugation at 300 μg for 10 minutes at 4° C., and were re-suspended in PBS. Then, the cells from each sample were divided into three aliquots: one was used in cytometry; another was used in RT-qPCR; and the rest was mixed with cryo-protectant (80% FBS and 20% DMSO) at 1:1 ratio, and stored in liquid nitrogen. The cells used for cytometry were incubated with 0, 0.5, 1, and 5 μM PDCy3, respectively, on ice for 20 minutes in the dark, and then were analyzed by flowcytometry.

RT-qPCR analysis. Cells collected from each urine sample were centrifuged at 300 μg for 10 minutes at 4° C., and then were re-suspended in 1 mL Trizol. After sitting at RT for 5 minutes, 0.25 mL chloroform was added into each sample. After incubation at RT for 5 minutes, the samples were centrifuged at 13,700 μg for 15 minutes at 4° C., and the aqueous phase from each sample was collected individually and mixed with isopropanol at 1:1 (v/v) ratio. After sitting at −20° C. for 30 minutes, the samples were cleared by centrifugation at 13,700 μg for 15 minutes at 4° C., the supernatants were discarded, and the pellets were washed with 75% ethanol. Then, the pellets were air-dried for half an hour and dissolved in 20 μL DEPC-treated $H_2O$, separately.

The reverse transcription of extracted RNA and q-PCR quantification of gene expression were carried out as described by the manufacture using the Transcriptor First Strand cDNA Synthesis kit and the FastStart Essential DNA Green Master kit, respectively (Roche, USA). The primers used in the experiments were listed in the Table 1. The expression of each gene from each subject was determined by q-PCR analysis using a LightCycler-96 machine. Experimental statistics were determined by using triplicated samples of extracted RNA.

TABLE 1

Primers used in q-PCR analysis

| Primer | Sequence | SEQ ID NO: |
|---|---|---|
| EGFR-Forward | CCCACTCATGCTCTACAACCC | 1 |
| EGFR-Reverse | TCGCACTTCTTACACTTGCGG | 2 |
| HER2-Forward | TGTGACTGCCTGTCCCTA-CAAC | 3 |
| HER2-Reverse | CCAGACCATAGCACACTCGG | 4 |
| β-actin-Forward | GGGACCTGACTGACTACCTC | 5 |
| β-actin-Reverse | TCATACTCCTGCTTGCTGAT | 6 |
| GAPDH-Forward | ATCATCCCTGCCTCTACTGG | 7 |
| GAPDH-Reverse | GTCAGGTCCACCACTGACAC | 8 |

HE Staining. After deparaffinization and rehydration, 5 μm-long sections were stained with hematoxylin solution for 5 minutes followed by dipping in 1% acid ethanol (1% HCl, 70% ethanol) 5 times. The sections were rinsed with distilled water, stained with eosin solution for 3 minutes, dehydrated with graded alcohol, and cleared in xylene. The mounted slides were examined and photographed using a Leica DM2500 microscope.

Immunohistochemistry. Formalin-fixed, paraffin-embeded (FFPE) sections were deparaffinized and blocked with 3% $H_2O_2$. Antigen retrieval was carried out twice in 0.01 M citrate for 10 minutes each using a microwave, and the sections were cooled down for 60 minutes. The slides were blocked with 3% goat serum and labelled separately with various primary antibodies. Then, the slides were labelled with secondary antibodies conjugated to Envision-plus HRP-labelled polymer and stained with DAB staining solution (Zhong Shan gold bridge, Beijing). Counterstaining was performed using Mayer-hematoxylin.

Ethics statement. Informed consent was obtained from each enrolled patient. This study was approved by the ethics board of The Second Hospital of Tianjin Medical University (Certificate #KY2017K010).

Results

Competitive Inhibition of the EGFR Kinase Activity

The functions of each module of the probe were analyzed individually. Overall, the fluorescent spectrum of our synthesized probe was quite similar to that of Cy3, except an additional minor peak at 674 nm appeared in the emission spectrum (FIG. 2A). This additional minor peak in the emission spectrum could extend the detectable range of PDCy3 to visible red and near infrared region in imaging applications, such as FRET and in vivo imaging experiments.

Then, we analyzed the inhibitory effects of PDCy3 on EGFR kinase activity (FIG. 2B). In the assay, EGFR-transfected HEK293T cells were treated with PDCy3 at different concentrations for 10 minutes in the presence or absence of 10 nM EGF. The expression and phosphorylation levels of EGFR were detected and analyzed by western blotting. As shown in the FIG. 2B, the probe could inhibit the kinase activity of EGFR in a dose dependent manner. Complete inhibition of EGFR kinase activity was achieved at the probe concentration of 20 μM. In comparison, the kinase activity of EGFR was completely inhibited by 5 μM gefitinib under the same condition (FIG. 2B).

Using gefitinib as a competitor[52], we confirmed the inhibitory specificity of PDCy3 on EGFR kinase activity (FIG. 2C). EGFR- or mock transfected cells were simultaneously labeled with EGFR-specific antibody 528 and PDCy3 in the presence or absence of 5 μM gefitinib. The binding abilities of PDCy3 to EGFR-expressed and non-expressed cells were compared by flowcytometry under different conditions. Treatment with 10 nM EGF did not enhance the binding of PDCy3 to EGFR-expressed cells (FIG. 2C). However, in the presence of EGF, adding 5 M gefitinib reduces the fraction of EGFR-expressed, PDCy3 positive cells relative to the total EGFR-expressed cells from 24.9% to 8.1% (FIG. 2C). In addition, the relative bound PDCy3 were reduced from 45.4 a.u. to 5.3 a.u. (FIG. 2D, a.u., arbitrary unit, which is defined as the mean fluorescent intensity of $PDCy3^+/EGFR^+$ cells times the fraction of $PDCy3^+/EGFR^+$ cells relative to the total $EGFR^+$ cells). These results suggested that PDCy3 could specifically inhibit the kinase activity of EGFR and a known EGFR inhibitor could competitively block PDCy3 binding to the receptor. From another point of view, this experiment demonstrated the utility of PDCy3 in screening of EGFR inhibitors by competition.

Sensitive to Oncogenic EGFR Mutation but not Asymmetric Kinase Dimerization

To characterize the specificity of PDCy3, we compared the efficiencies in labelling EGFR over-expressed cells versus those non-over-expressed cells under different PDCy3 concentrations (FIG. 3A). We found that transfected EGFR-positive cells could be specifically labelled by PDCy3 under 1 M concentration. Under this condition, over 84.9% EGFR positive cells could be labeled by this probe. In comparison, 6.7% EGFR negative cells and 1.4% mock transfected cells were labelled by PDCy3 at the same condition. However, when the concentration of PDCy3 was increased to 5 μM or higher, mock transfected cells or transfected, EGFR-negative cells were starting to be labelled non-specifically.

As PDCy3 was derived from PD168393, which was compatible with the active and inactive conformations of the EGFR kinase and was able to promote EGFR dimerization on cell surface in the absence of EGF 50, s we studied whether this probe would be more sensitive to EGFR oncogenic mutation or to EGFR asymmetric kinase dimerization[54] (FIG. 3B). Introduction of L834R mutation, which could destabilize the inactive conformation of EGFR kinase[55], increased the fraction of PDCy3-bound, EGFR positive cells from 52.4% to 65.9% (FIG. 3B, 3C). Disruption of the asymmetric kinase dimer by V924R mutation did not impair the binding of PDCy3 to transfected EGFR positive cells, but rather enhance the fraction of PDCy3-bound cells by 8% (FIG. 3B, 3C).

To further investigate how EGFR kinase dimerization affects PDCy3 binding, we carried out a protein complementary assay. In the assay, split YFP fragments were individually fused to the C-termini of EGFRs, and the kinase dimerization was reported by the fluorescence of assembled YPF from co-transfected, dimerized receptors (FIG. 4A)[56]. As shown in the FIG. 4B, the cells with co-expressed EGFR-YFP dimers could be divided into two populations (FIG. 4B, as denoted as population A and B). In population A, the quantity of bound PDCy3 was higher and was increased linearly as a function of expressed EGFR dimers (FIG. 4C). In population B, the quantity of bound PDCy3 was lower and was independent of the expressed EGFR dimers. L858R mutation rendered both populations to be sensitive to PDCy3 binding (FIG. 4C). However, its population A, which is equivalent to the probe-sensitive population of the wild type (WT) receptor, is 5 times more sensitive than the population B in response to PDCy3 binding (FIG. 4C). In addition, compared with that of the WT receptor, the fraction of the population A decreased from 38.4% to 27.4% (FIG. 4D). On the other hand, V924R mutation did not block the dimerization of co-transfected L834R receptors, as determined by the formation of assembled EGFR-YFP dimer (FIG. 4B). Instead, it changed the probe binding to the population B to be independent of or inverse proportional to the expressed EGFR dimers (FIG. 4B, 4C). Moreover, V924R mutation increased the fraction of the population A from 27.4% to 49.2% (FIG. 4B, 4D). These results in together indicated that there were two different EGFR dimeric forms on the cell surface: one was highly sensitive to PDCy3 binding, but the other was not. As V924R mutation could disrupt the asymmetric kinase dimer[54], the dimer identified with high-sensitivity to PDCy3 is different from that asymmetric, active dimer.

Stratification of Prostate Cancers by Using the Probe-Based Cytometry

In two small cohort studies, it was estimated that over 30% prostate cancer patients associated with EGFR over-expression and about 10-15% patients associated with EGFR mutations 47,48. However, much remained unknown regarding the following questions. Are these expression or genetic alterations really associated with malfunctions of EGFR? How to effectively identify those patients with abnormally activated EGFR? How do EGFR malfunctions associate with the pathogenesis of prostate cancer? Which subgroup of patients could benefit from EGFR inhibitor treatment? As a forward step to understand these questions, we tested the possibility of using probe-based cytometry to classify prostate cancer patients according to the response of their urine samples to the binding of our designed probe. In total, seven prostate cancer patients had been enrolled in our small cohort study (Table 2). To avoid bias, clinical information of enrolled subjects were blinded to the biochemical and cell biology experimentalists until the end of all experiments and analysis.

TABLE 2

Clinical information of enrolled subjects

| Subject | Age | Gleason Scores | Diagnosis | Pathology | Treatment |
|---|---|---|---|---|---|
| 1 | 71 | 3 + 3 | Hematuria<br>Urine Cytology: tumor cells detected 3 times | Urothelial cell carcinoma<br>Prostate carcinoma | |
| 2 | 67 | 4 + 4 | tPSA 221 ng/mL<br>MRI: Prostate carcinoma | Prostate carcinoma | Hormone Deprivation Therapy: 3 months<br>Radical Prostatectomy |

TABLE 2-continued

Clinical information of enrolled subjects

| Subject | Age | Gleason Scores | Diagnosis | Pathology | Treatment |
|---|---|---|---|---|---|
| 3 | 63 | | tPSA > 120 ng/mL | Prostate carcinoma Bone metastasis | Goserlin + Bicalutamide: 14 months Abiraterone: >15 months |
| 4 | 67 | | tPSA 395 ng/mL | Metastatic Prostate adeno-carcinoma Immunohistochemistry: AR(+), PSA(+), CK7(−), CK20(−), Villin(−) | Goserlin + Bicalutamide: 9 months Abiraterone: >3 months |
| 5 | 67 | 3 + 3 | tPSA 7.02 ng/mL fPSA 2.02 ng/mL MRI: Nodules in the apex of the prostate gland | Prostate carcinoma | Radical Prostatectomy |
| 6 | 70 | 4 + 4 | tPSA 10.9 ng/mL fPSA 0.61 ng/mL MRI: Nodules in the peripheral zone and apex of the prostate gland | Prostate carcinoma | Radical Prostatectomy |
| 7 | 71 | | tPSA 37.4 ng/mL fPSA 5.89 ng/mL Bone Scintigraphy: Unable to exclude bone metastasis | Prostate carcinoma Metastasis found in bilateral lymph nodes | Radical Prostatectomy |
| 8 | 69 | | MRI: Bladder carcinoma; Unable to exclude prostate carcinoma | Invasive urothelial carcinoma Immunohistochemistry: CK7(+), CK20 partial (+), P63(+), Ki-67 80% (+), GATA3(+) | Transurethral resection of bladder tumor |

The urine samples were labeled with 0.0, 0.5, 1.0, and 5.0 μM probe, respectively, at 4° C. for half an hour, and then were subjected to FACS analysis. Different cell populations could be distinguished by their side scattering and fluorescent intensity of bound probes (FIG. 6A). Moreover, samples collected from different subjects showed distinctive response profiles to the probe, which were presented as the relative bound probes as a function of the probe concentration (FIG. 6A, 6B). Especially, the sensitivity of the sample from subject 4 was significantly higher than the sensitivities of others (FIG. 6B). At 0.5 μM of the probe, the relative bound probe to this sample was 13.6 times higher than the average of others. In addition, the fractions of bound probe at 0.5 and 1.0 M concentration relative to the one at 5.0 μM concentration were 0.28 and 0.30, respectively. In contrast, the highest relative bound fractions at 0.5 and 1.0 μM probe from other samples were 0.1 and 0.16, respectively.

To gain further insights into the different response profiles of these samples in probe-based cytometry, we analyzed the expression and mutation status of these samples by RT-qPCR and Sanger sequencing (FIG. 6C, 6D, 7A, 7B). In RT-qPCR, the overexpression of EGFR were detected in all other samples, but not in those from subject 1 and subject 4 (FIG. 6C, 7A). In addition, three single nucleotide polymorphisms (SNPs) (V745M, G800D, and P770T) on EGFR kinase domain were identified in the sample from subject 4 but not in others by bi-directional Sanger sequencing (FIG. 6D, 7B). V745M mutation had been found in non-gefitinib treated lung cancer patients with uncertain significance[57], while G800D mutation had been identified in squamous cell carcinoma of head and neck and was indicated to be drug response with no criteria provided (https://www.ncbi.nlm-.nih.gov/clinvar/)[58]. P770T mutation had not been reported yet in cancer studies (https://www.ncbi.nlm.nih.gov/clinvar/). So we tested the kinase activities and probe responses of these mutations (FIG. 6E-G, 7C). In transiently transfected 293T cells, the kinase activity of V745M mutant was higher than that of the WT receptor, but the kinase activities of G800D, P770T, and other combinational mutants were impaired to certain extends (FIG. 6G). Consistent with their kinase activities, the cells transfected with the V745M mutant and the WT receptor exhibited high sensitivity to PDCy3 in flowcytometry, but the cells transfected with G800D, P770T, and their combinations did not respond to the probe (FIG. 6E, 6F, 7C). Collectively, these results suggested that activating mutation of EGFR on V745M accounted for the enhanced sensitivity of the sample from subject 4 to the probe.

Examining the biopsy specimen from subject 4 confirmed that the patient had metastatic prostate adenocarcinoma with overexpressed androgen receptor (FIG. 6H, 6I, 8). Later retrospective review found the case was castration-resistant (Table 2).

Discussion

Effective stratification of patients is critical in the diagnosis and treatment of prostate cancer[34]. Currently, tissue specimen examination and genetic profiling are widely used in clinical studies. However, abnormal variations on genetic, immunologic, or metabolic biomarkers, as detected by these techniques, are not equivalent to personalized pharmaceutic response to a potential or applied therapeutic agent. Yet, enormous genetic and epigenetic variations associated with tumor heterogeneity and mutational burden are still not fully appreciated[59]. These limitations hindered the development of novel therapeutic strategies and complicated our understanding of how to correlate genetic analysis to clinical applications[59]. Our chemical stratification strategy comes to the point on detecting personalized drug response using body fluid from individual patient and subtyping patients accordingly. By using this liquid biopsy technique in a small cohort study, we identified one prostate cancer patient with high sensitivity to our designed theranostic probe carrying an EGFR activating mutation (V745M) and having metastatic tumor. In the same patient, two more accompany, inactivating mutations (G800D and P770T) were also identified, indicating increased mutational frequency or heterogeneity associated with cancer progression. In addition, we found those patients who had overexpressed WT EGFR did not exhibit high sensitivity to the probe, in concert with the reports from early multicenter clinical studies[49]. We envisioned that chemical stratification combined with liquid biopsy could be complimentary to genetic profilings in the future clinical studies.

Our chemical stratification was established on our modular design of theranostic probes targeting EGFR kinase in specific conformations associated with oncogenesis. In our structure-based design, we explored the potentials in reprograming the verified EGFR kinase inhibitors for applications in drug screening, cell sorting, and imaging of protein interactions. The benefits of our modular design include, but not limited to, the exchangeable imaging and targeting modules. The exchangeable imaging module could be used at different biological and/or therapeutic settings with their different imaging properties. On the other hand, the exchangeable targeting module could be used for detecting other targets or other states of a specific target. In our case, PDCy3 was selective for EGFR overexpressing cells and was more sensitive to EGFR activating mutations, including L834R, a well-characterized mutation, and V745M, a mutation identified in this study.

Based on their sensitivities to PDCy3 binding, two different cell populations representing different EGFR dimers were identified on cell surface. In these two populations, one was highly sensitive to PDCy3 binding, but the other was not. L834R mutation promoted the formation of dimers with weak sensitivity to PDCy3 binding, while V924R mutation stimulated the formation of dimers with high sensitivity to PDCy3. Considering that V924R mutation could disrupt the asymmetric, active EGFR kinase dimer and L834R favors the active conformation of the kinase[54, 60], the EGFR dimers with weak sensitivity to PDCy3 represent the asymmetric, active kinase dimers. On the other side, the EGFR dimers with high sensitivity to PDCy3 actually represent another kinase association state. From early structural studies, it had been proposed that EGFR kinase domain was capable of forming both the asymmetric, active dimer and the symmetric, inactive dimer in vitro[54, 61]. Intuitively, it is possible that PDCy3-sensitive dimer was equivalent or related to the symmetric, inactive kinase dimer. However, many evidences argued against that possibility. In our experiments, we found EGFR activating mutations, including L834R and V745M, promoted the binding of PDCy3 to EGFR-expressed cells. However, inactivating mutations, including G800D and P770T, lowered or abolished the binding of PDCy3 to those cells. At the same time, disruption of the asymmetric, active kinase dimer by V924R mutation enhanced the binding of PDCy3 to EGFR-expressed cells. These results indicated that the PDCy3 preferred to bind non-asymmetrically associated, non-inactive EGFR kinase. It had also been shown that gefitinib and PD168393, being compatible with both active and inactive conformations of EGFR kinase, could drive the homo- or hetero-dimerization of unligated EGFRs on cell surface[50, 62]. In contrast, lapatinib and HKI-272, both stabilizing the kinase in inactive conformation, failed to do so[50]. Such disparity had been attributed to the conformational, dynamic nature of the kinase[53, 63] Indeed, intermediate transition states of the EGFR kinase had been identified in molecular dynamic simulation[64, 65]. It is intriguing to note that the available structures of PD168393-bound EGFR kinases varied largely at their N-lobe and α-C helix positioning (r.m.s.d. varies from 1.8 Å to 2.7 Å, when they were superimposed on their C-lobes) (FIG. 5A)[66, 67] And one of these structures (PDB 4LL0) is more close to the intermediate state identified in molecular dynamic simulation with intrinsically disordered α-C helix (PDB 2RF9) (FIG. 5B)[64]. Nevertheless, our probe and protein complementary assay provided a tool for dissecting EGFR dimerization and drug sensitivity. Our results indicated that there were two different dimeric kinase populations co-existed on cell surface. These two different dimerization states associated with different sensitivities to kinase inhibitors.

REFERENCES

1. Bray, F. et al. Global cancer statistics 2018: GLOBOCAN estimates of incidence and mortality worldwide for 36 cancers in 185 countries. CA Cancer J Clin (2018).
2. Qian, W., Zhang, Y. & Chen, W. Capturing Cancer: Emerging Microfluidic Technologies for the Capture and Characterization of Circulating Tumor Cells. Small 11, 3850-3872 (2015).
3. Rawal, S., Yang, Y. P., Cote, R. & Agarwal, A. Identification and Quantitation of Circulating Tumor Cells. Annu Rev Anal Chem (Palo Alto Calif) 10, 321-343 (2017).
4. Kowalik, A., Kowalewska, M. & Gozdz, S. Current approaches for avoiding the limitations of circulating tumor cells detection methods-implications for diagnosis and treatment of patients with solid tumors. Transl Res 185, 58-84 e15 (2017).
5. Gorin, M. A. et al. Circulating tumour cells as biomarkers of prostate, bladder, and kidney cancer. Nat Rev Urol 14, 90-97 (2017).
6. Singh, A. P., Li, S. & Cheng, H. Circulating DNA in EGFR-mutated lung cancer. Ann Transl Med 5, 379 (2017).
7. Kobayashi, S. et al. EGFR mutation and resistance of non-small-cell lung cancer to gefitinib. N Engl J Med 352, 786-792 (2005).
8. Shih, J. Y., Gow, C. H. & Yang, P. C. EGFR mutation conferring primary resistance to gefitinib in non-small-cell lung cancer. N Engl J Med 353, 207-208 (2005).
9. Paez, J. G. et al. EGFR mutations in lung cancer: correlation with clinical response to gefitinib therapy. Science 304, 1497-1500 (2004).
10. Lynch, T. J. et al. Activating mutations in the epidermal growth factor receptor underlying responsiveness of non-small-cell lung cancer to gefitinib. N Engl J Med 350, 2129-2139 (2004).
11. Pao, W. & Miller, V. A. Epidermal growth factor receptor mutations, small-molecule kinase inhibitors, and non-small-cell lung cancer: current knowledge and future directions. J Clin Oncol 23, 2556-2568 (2005).

12. da Cunha Santos, G., Shepherd, F. A. & Tsao, M. S. EGFR mutations and lung cancer. Annu Rev Pathol 6, 49-69 (2011).
13. Kovacs, E., Zorn, J. A., Huang, Y., Barros, T. & Kuriyan, J. A structural perspective on the regulation of the epidermal growth factor receptor. Annu Rev Biochem 84, 739-764 (2015).
14. Lemmon, M. A., Schlessinger, J. & Ferguson, K. M. The EGFR family: not so prototypical receptor tyrosine kinases. Cold Spring Harb Perspect Biol 6, a020768 (2014).
15. Zhang, X., Gureasko, J., Shen, K., Cole, P. A. & Kuriyan, J. An allosteric mechanism for activation of the kinase domain of epidermal growth factor receptor. Cell 125, 1137-1149 (2006).
16. Jura, N. et al. Mechanism for activation of the EGF receptor catalytic domain by the juxtamembrane segment. Cell 137, 1293-1307 (2009).
17. Eck, M. J. & Yun, C. H. Structural and mechanistic underpinnings of the differential drug sensitivity of EGFR mutations in non-small cell lung cancer. Biochim Biophys Acta 1804, 559-566 (2010).
18. Blair, J. A. et al. Structure-guided development of affinity probes for tyrosine kinases using chemical genetics. Nat Chem Biol 3, 229-238 (2007).
19. Yun, C. H. et al. The T790M mutation in EGFR kinase causes drug resistance by increasing the affinity for ATP. Proc Natl Acad Sci USA 105, 2070-2075 (2008).
20. Lu, C., Mi, L. Z., Schurpf, T., Walz, T. & Springer, T. A. Mechanisms for kinase-mediated dimerization of the epidermal growth factor receptor. J Biol Chem 287, 38244-38253 (2012).
21. Park, J. H., Liu, Y., Lemmon, M. A. & Radhakrishnan, R. Erlotinib binds both inactive and active conformations of the EGFR tyrosine kinase domain. Biochem J 448, 417-423 (2012).
22. Yun, C. H. et al. Structures of lung cancer-derived EGFR mutants and inhibitor complexes: mechanism of activation and insights into differential inhibitor sensitivity. Cancer Cell 11, 217-227 (2007).
23. Shyu, Y. J., Liu, H., Deng, X. & Hu, C. D. Identification of new fluorescent protein fragments for bimolecular fluorescence complementation analysis under physiological conditions. Biotechniques 40, 61-66 (2006).
24. Zhang, X. et al. Inhibition of the EGF receptor by binding of MIG6 to an activating kinase domain interface. Nature 450, 741-744 (2007).
25. Anido, J. et al. ZD1839, a specific epidermal growth factor receptor (EGFR) tyrosine kinase inhibitor, induces the formation of inactive EGFR/HER2 and EGFR/HER3 heterodimers and prevents heregulin signaling in HER2-overexpressing breast cancer cells. Clin Cancer Res 9, 1274-1283 (2003).
26. Barkovich, K. J. et al. Kinetics of inhibitor cycling underlie therapeutic disparities between EGFR-driven lung and brain cancers. Cancer Discov 2, 450-457 (2012).
27. Shan, Y. et al. Oncogenic mutations counteract intrinsic disorder in the EGFR kinase and promote receptor dimerization. Cell 149, 860-870 (2012).
28. Shan, Y., Arkhipov, A., Kim, E. T., Pan, A. C. & Shaw, D. E. Transitions to catalytically inactive conformations in EGFR kinase. Proc Natl Acad Sci USA 110, 7270-7275 (2013).
29. Red Brewer, M. et al. Mechanism for activation of mutated epidermal growth factor receptors in lung cancer. Proc Natl Acad Sci USA 110, E3595-3604 (2013).
30. Yasuda, H. et al. Structural, biochemical, and clinical characterization of epidermal growth factor receptor (EGFR) exon 20 insertion mutations in lung cancer. Sci Transl Med 5, 216ra177 (2013).
31. Bray, F. et al. Global cancer statistics 2018: GLOBOCAN estimates of incidence and mortality worldwide for 36 cancers in 185 countries. CA Cancer J Clin 68, 394-424, doi:10.3322/caac.21492 (2018).
32. Siegel, R. L., Miller, K. D. & Jemal, A. Cancer statistics, 2018. CA Cancer J Clin 68, 7-30, doi:10.3322/caac.21442 (2018).
33. Streicher, J., Meyerson, B. L., Karivedu, V. & Sidana, A. A review of optimal prostate biopsy: indications and techniques. Ther Adv Urol 11, 1756287219870074, doi:10.1177/1756287219870074 (2019).
34. Litwin, M. S. & Tan, H. J. The Diagnosis and Treatment of Prostate Cancer: A Review. JAMA 317, 2532-2542, doi:10.1001/jama.2017.7248 (2017).
35. Parikh, A. R. et al. Liquid versus tissue biopsy for detecting acquired resistance and tumor heterogeneity in gastrointestinal cancers. Nat Med 25, 1415-1421, doi:10.1038/s41591-019-0561-9 (2019).
36. Qian, W., Zhang, Y. & Chen, W. Capturing Cancer: Emerging Microfluidic Technologies for the Capture and Characterization of Circulating Tumor Cells. Small 11, 3850-3872, doi:10.1002/smll.201403658 (2015).
37. Rawal, S., Yang, Y. P., Cote, R. & Agarwal, A. Identification and Quantitation of Circulating Tumor Cells. Annu Rev Anal Chem (Palo Alto Calif) 10, 321-343, doi:10.1146/annurev-anchem-061516-045405 (2017).
38. Kowalik, A., Kowalewska, M. & Gozdz, S. Current approaches for avoiding the limitations of circulating tumor cells detection methods-implications for diagnosis and treatment of patients with solid tumors. Transl Res 185, 58-84 e15, doi:10.1016/j.trsl.2017.04.002 (2017).
39. Gorin, M. A. et al. Circulating tumour cells as biomarkers of prostate, bladder, and kidney cancer. Nat Rev Urol 14, 90-97, doi:10.1038/nrurol.2016.224 (2017).
40. Labib, M. et al. Single-cell mRNA cytometry via sequence-specific nanoparticle clustering and trapping. Nat Chem 10, 489-495, doi:10.1038/s41557-018-0025-8 (2018).
41. Singh, A. P., Li, S. & Cheng, H. Circulating DNA in EGFR-mutated lung cancer. Ann Transl Med 5, 379, doi:10.21037/atm.2017.07.10 (2017).
42. Kobayashi, S. et al. EGFR mutation and resistance of non-small-cell lung cancer to gefitinib. N Engl J Med 352, 786-792, doi:10.1056/NEJMoa044238 (2005).
43. Shih, J. Y., Gow, C. H. & Yang, P. C. EGFR mutation conferring primary resistance to gefitinib in non-small-cell lung cancer. N Engl J Med 353, 207-208, doi:10.1056/NEJM200507143530217 (2005).
44. Paez, J. G. et al. EGFR mutations in lung cancer: correlation with clinical response to gefitinib therapy. Science 304, 1497-1500, doi:10.1126/science.1099314 (2004).
45. Lynch, T. J. et al. Activating mutations in the epidermal growth factor receptor underlying responsiveness of non-small-cell lung cancer to gefitinib. N Engl J Med 350, 2129-2139, doi:10.1056/NEJMoaO40938 (2004).
46. Shah, R. B., Ghosh, D. & Elder, J. T. Epidermal growth factor receptor (ErbB1) expression in prostate cancer progression: correlation with androgen independence. Prostate 66, 1437-1444, doi:10.1002/pros.20460 (2006).
47. Peraldo-Neia, C. et al. Epidermal Growth Factor Receptor (EGFR) mutation analysis, gene expression profiling and EGFR protein expression in primary prostate cancer.

BMC Cancer 11, 31, doi:10.1186/1471-2407-11-31 (2011).
48. Cho, K. S. et al. Gene amplification and mutation analysis of epidermal growth factor receptor in hormone refractory prostate cancer. Prostate 68, 803-808, doi: 10.1002/pros.20743 (2008).
49. Sridhar, S. S. et al. A multicenter phase II clinical trial of lapatinib (GW572016) in hormonally untreated advanced prostate cancer. Am J Clin Oncol 33, 609-613, doi:10.1097/COC.0b013e3181beac33 (2010).
50. Lu, C., Mi, L. Z., Schurpf, T., Walz, T. & Springer, T. A. Mechanisms for kinase-mediated dimerization of the epidermal growth factor receptor. J Biol Chem 287, 38244-38253, doi:10.1074/jbc.M112.414391 (2012).
51. Mi, L. Z. et al. Simultaneous visualization of the extracellular and cytoplasmic domains of the epidermal growth factor receptor. Nat Struct Mol Biol 18, 984-989, doi:10.1038/nsmb.2092 (2011).
52. Yun, C. H. et al. The T790M mutation in EGFR kinase causes drug resistance by increasing the affinity for ATP. Proc Natl Acad Sci USA 105, 2070-2075, doi:10.1073/pnas.0709662105 (2008).
53. Park, J. H., Liu, Y., Lemmon, M. A. & Radhakrishnan, R. Erlotinib binds both inactive and active conformations of the EGFR tyrosine kinase domain. Biochem J 448, 417-423, doi:10.1042/BJ20121513 (2012).
54. Zhang, X., Gureasko, J., Shen, K., Cole, P. A. & Kuriyan, J. An allosteric mechanism for activation of the kinase domain of epidermal growth factor receptor. Cell 125, 1137-1149, doi:10.1016/j.cell.2006.05.013 (2006).
55. Yun, C. H. et al. Structures of lung cancer-derived EGFR mutants and inhibitor complexes: mechanism of activation and insights into differential inhibitor sensitivity. Cancer Cell 11, 217-227, doi:10.1016/j.ccr.2006.12.017 (2007).
56. Shyu, Y. J., Liu, H., Deng, X. & Hu, C. D. Identification of new fluorescent protein fragments for bimolecular fluorescence complementation analysis under physiological conditions. Biotechniques 40, 61-66, doi:10.2144/000112036 (2006).
57. Huang, S. F. et al. High frequency of epidermal growth factor receptor mutations with complex patterns in non-small cell lung cancers related to gefitinib responsiveness in Taiwan. Clin Cancer Res 10, 8195-8203, doi:10.1158/1078-0432.CCR-04-1245 (2004).
58. Nagalakshmi, K., Jamil, K., Pingali, U., Reddy, M. V. & Attili, S. S. V. Epidermal growth factor receptor (EGFR) mutations as biomarker for head and neck squamous cell carcinomas (HNSCC). Biomarkers 19, 198-206, doi: 10.3109/1354750x.2014.895852 (2014).
59. Buisson, R. et al. Passenger hotspot mutations in cancer driven by APOBEC3A and mesoscale genomic features. Science 364, doi:10.1126/science.aaw2872 (2019).
60. Zhang, X. et al. Inhibition of the EGF receptor by binding of MIG6 to an activating kinase domain interface. Nature 450, 741-744, doi:10.1038/nature05998 (2007).
61. Jura, N. et al. Mechanism for activation of the EGF receptor catalytic domain by the juxtamembrane segment. Cell 137, 1293-1307, doi:10.1016/j.cell.2009.04.025 (2009).
62. Anido, J. et al. ZD1839, a specific epidermal growth factor receptor (EGFR) tyrosine kinase inhibitor, induces the formation of inactive EGFR/HER2 and EGFR/HER3 heterodimers and prevents heregulin signaling in HER2-overexpressing breast cancer cells. Clin Cancer Res 9, 1274-1283 (2003).
63. Barkovich, K. J. et al. Kinetics of inhibitor cycling underlie therapeutic disparities between EGFR-driven lung and brain cancers. Cancer Discov 2, 450-457, doi: 10.1158/2159-8290.CD-11-0287 (2012).
64. Shan, Y. et al. Oncogenic mutations counteract intrinsic disorder in the EGFR kinase and promote receptor dimerization. Cell 149, 860-870, doi:10.1016/j.cell.2012.02.063 (2012).
65. Shan, Y., Arkhipov, A., Kim, E. T., Pan, A. C. & Shaw, D. E. Transitions to catalytically inactive conformations in EGFR kinase. Proc Natl Acad Sci USA 110, 7270-7275, doi:10.1073/pnas.1220843110 (2013).
66. Red Brewer, M. et al. Mechanism for activation of mutated epidermal growth factor receptors in lung cancer. Proc Natl Acad Sci USA 110, E3595-3604, doi:10.1073/pnas.1220050110 (2013).
67. Yasuda, H. et al. Structural, biochemical, and clinical characterization of epidermal growth factor receptor (EGFR) exon 20 insertion mutations in lung cancer. Sci Transl Med 5, 216ra177, doi: 10.1126/scitranslmed.3007205 (2013).

The invention claimed is:

1. A theranostic probe represented by formula (1):

Module 2-L-Module 1 (1)

wherein

L is a linker;

Module 1 is a moiety targeting the EGFR kinase and is represented by formula (2):

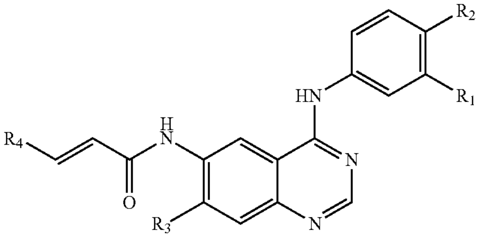

wherein $R_1$ in formula (2) is H, halogen or $C_{2-6}$alkynyl;

$R_2$ in formula (2) is H, halogen, $C_{6-10}$aryl$C_{1-6}$ alkyloxy or 5- to 6-membered heteroaryl$C_{1-6}$alkyloxy, wherein the $C_{6-10}$aryl and 5- to 6-membered heteroaryl are optionally substituted with halogen, and the 5- to 6-membered heteroaryl comprises 1, 2, 3 or 4 heteroatoms selected from the group consisting of O, S and N;

$R_3$ in formula (2) is H, $C_{1-6}$alkyloxy optionally substituted with $C_{1-6}$alkyloxy, or 5- to 6-membered heterocycloalkyloxy, wherein the 5- to 6-membered heterocycloalkyl comprises 1 or 2 heteroatoms selected from the group consisting of O, S and N;

$R_4$ in formula (2), as the attachment point of Module 1 to L, is $—(CH_2)_n—$; and n in formula (2) is 0, 1, 2, 3, 4, 5 or 6; and Module 2 is an imaging probe selected from the group consisting of fluorescent, MRI and radioactive probes;

or a theranostically acceptable salt thereof.

2. The theranostic probe of claim 1, wherein L is —C(O)O— or —C(O)NH—.

3. The theranostic probe of claim 1, wherein Module 2 is represented by formula (3) or (4):

(3)

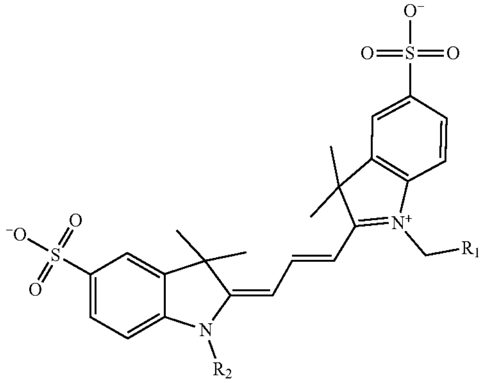

-continued (4)

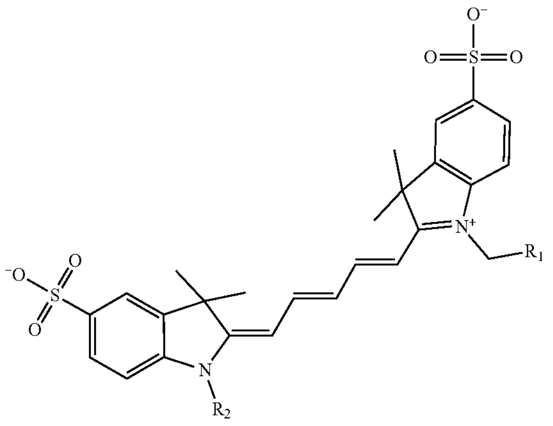

wherein $R_1$ in formula (3) or (4), as the attachment point of Module 2 to L, is $—(CH_2)_n—$;

$R_2$ in formula (3) or (4) is $—(CH_2)_nCH_3$; and n in formula (3) or (4), at each occurrence, is independently 0, 1, 2, 3, 4, 5 or 6;

or Module 2 is represented by formula (5) or (6):

$^{18}FCH_2—(CH_2)_n—*$ (5)

(6)

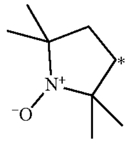

wherein the symbol * in formula (5) or (6) represents the attachment point of Module 2 to L; and n in formula (5) is independently 0, 1, 2, 3, 4, 5 or 6, wherein if necessary, a counterion is present and selected from the group consisting of alkali metal and alkaline earth metal ions.

4. The theranostic probe of claim 1, represented by formula (7):

(7)

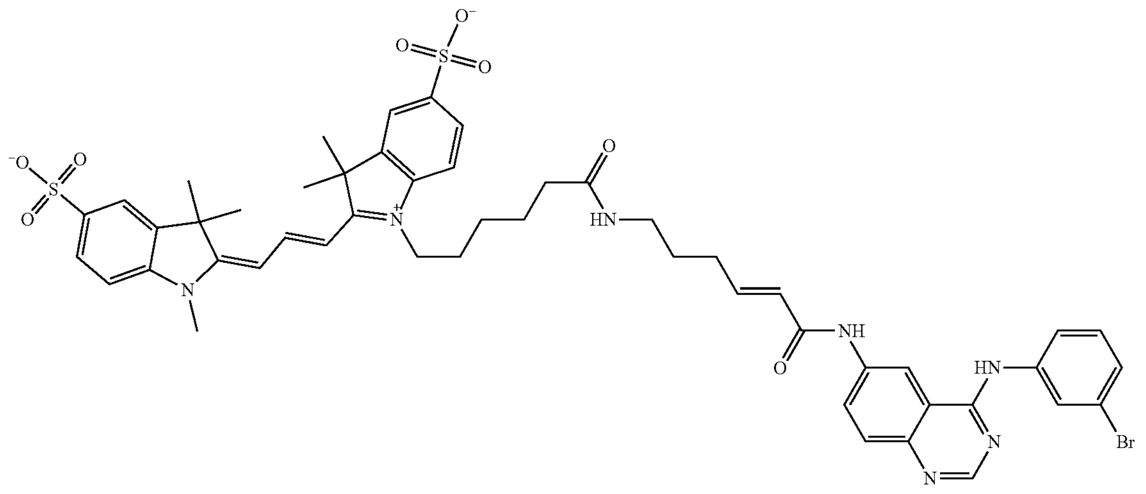

wherein a counterion is present and selected from the group consisting of alkali metal and alkaline earth metal ions.

5. The theranostic probe of claim 1, wherein the EGFR kinase has a mutation of L834R, V924R, V745M or combination of any two or three of L834R, V924R and V745M.

6. The theranostic probe of claim 1, wherein the EGFR kinase is present in a dimeric conformation.

7. The theranostic probe of claim 1, wherein the conformation of the EGFR kinase is associated with oncogenesis.

8. The theranostic probe of claim 1, wherein the conformation of the EGFR kinase is associated with prostate cancer.

9. The theranostic probe of claim 1, wherein the conformation of the EGFR kinase is associated with metastatic and/or castration-resistant prostate cancer.

* * * * *